(12) United States Patent
Antonsson

(10) Patent No.: US 6,221,898 B1
(45) Date of Patent: Apr. 24, 2001

(54) AMIDINO DERIVATIVES AND THEIR USE AS THROMBIN INHIBITORS

(75) Inventor: Thomas Antonsson, Lindome (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 08/894,833

(22) PCT Filed: Jun. 26, 1997

(86) PCT No.: PCT/SE97/01150

§ 371 Date: Aug. 29, 1997

§ 102(e) Date: Aug. 29, 1997

(87) PCT Pub. No.: WO98/01422

PCT Pub. Date: Jan. 15, 1998

(30) Foreign Application Priority Data

Jul. 4, 1996 (SE) .................................................... 9602646

(51) Int. Cl.[7] .................................................... A61K 31/38

(52) U.S. Cl. .................... 514/445; 514/535; 514/604; 514/506; 514/562; 514/255; 514/317; 514/330; 514/331; 544/398; 544/399; 544/400; 544/402; 546/21; 546/229; 546/230; 546/231; 560/13; 549/65; 564/15; 564/92; 562/431; 558/58

(58) Field of Search .................................................... 514/255, 317, 514/330, 331, 445, 535, 604, 506, 562; 544/398, 399, 400, 402; 546/21, 229, 230, 231; 504/237; 560/13; 549/65; 564/92, 15; 558/58; 562/431

(56) References Cited

U.S. PATENT DOCUMENTS

| | | |
|---|---|---|
| 4,346,078 | 8/1982 | Bajusz et al. . |
| 5,561,146 | 10/1996 | Kim et al. . |
| 5,583,146 | 12/1996 | Kimball et al. . |
| 5,602,253 | 2/1997 | Antonsson et al. . |
| 5,614,499 | 3/1997 | Bylund et al. . |
| 5,629,324 | 5/1997 | Vacca et al. . |
| 5,705,487 | 1/1998 | Schacht et al. . |
| 5,707,966 | 1/1998 | Schacht et al. . |
| 5,710,130 | 1/1998 | Schacht et al. . |
| 5,723,444 | 3/1998 | Antonsson et al. . |
| 5,726,159 | 3/1998 | Schacht et al. . |
| 5,741,792 | 4/1998 | Kimball et al. . |
| 5,741,799 | 4/1998 | Kimball et al. . |
| 5,744,487 | 4/1998 | Ohshima et al. . |
| 5,780,631 | 7/1998 | Antonsson et al. . |
| 5,783,563 | 7/1998 | Antonsson et al. . |
| 5,792,769 | 8/1998 | Lu et al. . |
| 6,034,127 | 3/2000 | Lu et al. . |
| 6,133,315 | 10/2000 | Lu et al. . |

FOREIGN PATENT DOCUMENTS

| | | |
|---|---|---|
| 0 185 390 | 6/1986 | (EP) . |
| 0 195 212 A2 | 9/1986 | (EP) . |
| 0 293 881 A2 | 12/1988 | (EP) . |
| 0 362 002 | 4/1990 | (EP) . |
| 0 364 344 A2 | 4/1990 | (EP) . |
| 0 364 344 A3 | 4/1990 | (EP) . |
| 0 468 231 A2 | 1/1992 | (EP) . |
| 0 468 231 A3 | 1/1992 | (EP) . |
| 0 526 877 A2 | 2/1993 | (EP) . |
| 0 526 877 A3 | 2/1993 | (EP) . |
| 0 530 167 A1 | 3/1993 | (EP) . |
| 0 542 525 A2 | 5/1993 | (EP) . |
| 0 559 046 A1 | 9/1993 | (EP) . |
| 0 601 459 A2 | 6/1994 | (EP) . |
| 0 623 596 A1 | 11/1994 | (EP) . |
| 0 641 779 A1 | 3/1995 | (EP) . |
| 0 648 780 A1 | 4/1995 | (EP) . |
| 0 669 317 A1 | 8/1995 | (EP) . |
| 686 642 | 12/1995 | (EP) . |
| 93/11152 | 6/1993 | (WO) . |
| 93/16038 | 8/1993 | (WO) . |
| 93/18060 | 9/1993 | (WO) . |
| WO94/20467 | 9/1994 | (WO) . |
| 94/29336 | 12/1994 | (WO) . |
| 95/23609 | 9/1995 | (WO) . |
| 95/35309 | 12/1995 | (WO) . |
| 96/03374 | 2/1996 | (WO) . |
| 96/06832 | 3/1996 | (WO) . |
| 96/06849 | 3/1996 | (WO) . |
| WO96/16940 | 6/1996 | (WO) . |
| 96/25426 | 8/1996 | (WO) . |
| 96/32110 | 10/1996 | (WO) . |

(List continued on next page.)

OTHER PUBLICATIONS

Blomback et al, "Synthetic Peptides with Anticoagulant . . . ," Scand. J. clin. Lab. Invest. Suppl. 107, pp. 59–64 (1969).

Claeson, G., "Synthetic peptides and peptidomimetics as substrates . . . ," Blood Coagulation and Fibrinolysis, vol. 5, pp. 411–436 (1994).

von der Saal et al, "Derivatives of 4–Amino–Pyridine as . . . ," Bioorganic & Medicinal Chemistry Letters, vol. 7, No. 10, pp. 1283–1288 (1997).

Primary Examiner—Samuel Barts
(74) Attorney, Agent, or Firm—Nixon & Vanderhye

(57) ABSTRACT

There is provided compounds of formula I,

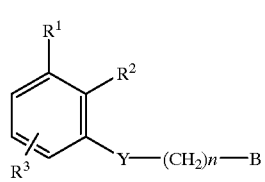

I wherein $R^1$, $R^2$, $R^3$, Y, n and B have meanings given in the description which are useful as competitive inhibitors of trypsin-like proteases, such as thrombin, and in particular in the treatment of conditions where inhibition of thrombin is required (e.g. thrombosis) or as anticoagulants.

31 Claims, No Drawings

FOREIGN PATENT DOCUMENTS

| | | |
|---|---|---|
| 96/37482 | 11/1996 | (WO) . |
| 97/11693 | 3/1997 | (WO) . |
| 97/02284 | 7/1997 | (WO) . |
| 97/23499 | 7/1997 | (WO) . |
| 97/24135 | 7/1997 | (WO) . |
| 97/47299 | 12/1997 | (WO) . |
| 98/01422 | 1/1998 | (WO) . |
| 98/06740 | 2/1998 | (WO) . |
| 98/06741 | 2/1998 | (WO) . |

AMIDINO DERIVATIVES AND THEIR USE AS THROMBIN INHIBITORS

FIELD OF THE INVENTION

This invention relates to novel pharmaceutically useful compounds, in particular competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would therefore be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P 1, hereinafter referred to as the P3-P2-P 1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position; European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609 and WO 94/29336.

Moreover, achiral thrombin inhibitors based on aminopyridine and aminopyridazine derivatives have recently been disclosed in International Patent Applications WO 94/20467, WO 96/06832 and WO 96/06849. Other achiral thrombin inhibitors have more recently been disclosed in Bioorg. Med. Chem. Lett. 7, 1283 (1997).

However, there remains a need for effective inhibitors of trypsin-like serine proteases, such as thrombin. There is a particular need for compounds which are both orally bio-available and selective in inhibiting thrombin over other serine proteases. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

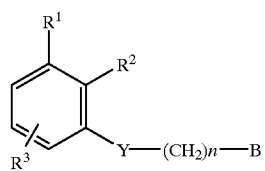

wherein
one of $R^1$ and $R^2$ represents a structural fragment of formula Ia

and the other represents $R^4$;

Z represents O or $N(R^5)$;

$R^3$ represents one or more optional substituents selected from OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;

$R^4$ represents H, OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;

$Ar^1$ represents phenyl, $C_{1-3}$alkylphenyl, $C_{1-3}$alkyldiphenyl, $C_{3-7}$cycloalkyl, $C_{1-3}$-alkyl-$C_{3-7}$-cycloalkyl, $C_{1-3}$-alkyl-di-$C_{3-7}$-cycloalkyl, naphthyl, $C_{1-3}$alkylnaphthyl, thienyl, imidazolyl or isoxazolyl, all of which may be substituted by one or more substituent selected from OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;

$R^5$ represents H, $C_{1-6}$alkyl, phenyl or $C_{1-3}$alkylphenyl (which three latter groups are optionally substituted and/or terminated by one or more substituent selected from OH, halo, cyano, nitro, $C(O)OR^9$, $C(O)N(R^{10})R^{11}$, $P(O)(R^{12})R^{13}$, $P(O)(OR^{14})OR^{15}$, $S(O)_2(R^{16})R^{17}$, $S(O)_2N(R^{18})R^{19}$, $C_{1-6}$alkoxy or $C_{1-6}$alkyl (which two latter groups are optionally substituted and/or terminated by one or more halo or hydroxy group) or $N(R^{20})R^{21}$);

Y represents O, S, S(O), $S(O)_2$ or $N(R^{22})$;

$R^{10}$ and $R^{11}$ independently represent H, $OR^{23}$, $C(O)R^{24}$, $OC(O)R^{25}$, $C(O)OR^{26}$, $C_{1-4}$alkyl, (which latter group is optionally substituted and/or terminated by one or more substituent selected from $C_{1-4}$alkyl, $OR^{27}$, $N(R^{28})R^{29}$, $C(O)OR^{30}$ $C(O)N(R^{31})R^{32}$, $P(O)(R^{33})R^{34}$, $P(O)(OR^{35})OR^{36}$ and $S(O)_2N(R^{37})R^{38}$), —(CH$_2$CH$_2$O—)$_p$R$^{39}$ or, together with the nitrogen atom to which they are attached, form a $C_{4-7}$ nitrogen-containing, aromatic or non-aromatic, ring which ring may contain a further heteroatom or group (as appropriate) selected from O, S and $N(R^{40})$ and may further be substituted by one or more substituent selected from $C(O)R^{41}$, $C(O)OR^{42}$ or $C(O)N(R^{43})R^{44}$;

$R^{28}$, $R^{29}$, $R^{30}$, $R^{31}$, $R^{32}$ and $R^{40}$ independently represent H or $C_{1-6}$alkyl, which latter group is optionally substituted and/or terminated by one or more substituent selected from $C(O)R^{45}$, $C(O)OR^{46}$ or $C(O)N(R^{47})R^{48}$; at each occurance, $R^6$, $R^7$ and $R^8$ independently represent H or $C_{1-4}$alkyl; $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{33}$, $R^{34}$, $R^{35}$, $R^{36}$, $R^{37}$, $R^{38}$, $R^{39}$, $R^{41}$, $R^{42}$, $R^{43}$, $R^{44}$, $R^{45}$, $R^{46}$, $R^{47}$ and $R^{48}$ independently represent H or $C_{1-4}$alkyl;

n represents 0, 1, 2, 3 or 4;

p represents 1, 2, 3, 4, 5 or 6; and

B represents a structural fragment of formula Ib, Ic, Id or Ie

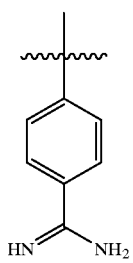

Ib

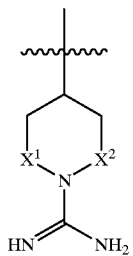

Ic

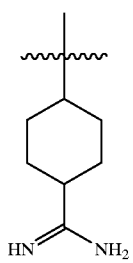

Id

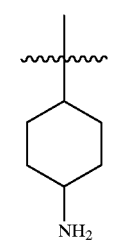

Ie wherein $X^1$ and $X^2$ independently represent a single bond or $CH_2$;

or a pharmaceutically acceptable salt thereof (hereinafter referred to as "the compounds of the invention").

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Alkyl groups which $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ may represent; the alkyl part of alkylphenyl, alkyldiphenyl, alkylcycloalkyl, alkyldicycloalkyl and alkylnaphthyl groups which $Ar^1$ may represent; the alkyl part of alkylphenyl groups which $R^5$ may represent; and alkoxy groups which $R^3$ and $R^4$ may represent, may be linear or branched, saturated or unsaturated, cyclic or acyclic. When $Ar^1$, $R^5$, $R^{10}$ or $R^{11}$ are substituted or terminated (as appropriate) by alkyl or alkoxy, such substituents may be linear or branched, saturated or unsaturated, cyclic or acyclic.

Halo groups which $R^3$ and $R^4$ may represent include fluoro, chloro, bromo and iodo. When $Ar^1$ and $R^1$ are substituted by halo, such substituents include fluoro, chloro, bromo and iodo.

The wavy lines on the carbon atom in the fragments of formulae Ia, Ib, Ic, Id and Ie signify the bond position of the fragment.

Abbreviations are listed at the end of this specification.

According to a further aspect of the invention there is provided a compound of formula I, as hereinbefore defined, provided that:

(a) $R^1$ represents a structural fragment of formula Ia and $R^2$ represents $R^4$;

(b) $Ar^1$ represents optionally substituted phenyl;

(c) $R^5$ is not substituted by $P(O)(OR^{14})OR^{15}$, $S(O)_2(R^{16})R^{17}$ or $S(O)_2N(R^{18})R^{19}$;

(d) $R^{10}$ and/or $R^{11}$ represent H or unsubstituted $C_{1-4}$alkyl;

(e) Y represents O, S or $N(R^5)$;

(f) B represents a structural fragment of formula Ib, Ic or Id.

According to a further aspect of the invention there is provided a compound of formula I, as hereinbefore defined, provided that:

(a) $R^2$ represents a structural fragment of formula Ia and $R^1$ represents $R^4$;

(b) $Ar^1$ does not represent optionally substituted phenyl;

(c) $R^5$ is substituted by $P(O)(OR^{14})OR^{15}$, $S(O)_2(R^{16})R^{17}$ or $S(O)_2N(R^{18})R^{19}$;

(d) $R^{10}$ and/or $R^{11}$ do not represent H or unsubstituted $C_{1-4}$alkyl;

(e) Y represents S(O) or $S(O)_2$;

(f) B represents a structural fragment of formula Ie.

When B represents a structural fragment of formula Ib, Id, Ie or Ic in which latter fragment $X^1$ and $X^2$ both represent $CH_2$, preferred compounds of the invention include those wherein n represents 2.

Preferred compounds of formula I include those wherein:

$R^1$ represents a structural fragment of formula Ia and $R^2$ represents $R^4$;

Z represents O or $N(R^5)$, in which latter case $R^5$ represents $C_{1-6}$alkyl substituted by $C(O)N(R^{10})R^{11}$;

$R^3$ is not present, or represents methyl, chloro or methoxy;

$Ar^1$ represents substituted phenyl;

Y represents O;

n represents 2;

B represents a structural fragment of formula Ib.

Preferred compounds of the invention include the compounds of Examples 1 to 55.

Preparation

According to the invention there is also provided a process for the preparation of compounds of formula I which comprises:

(a) reaction of a compound of formula II,

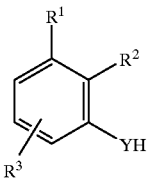

II wherein $R^1$, $R^2$, $R^3$ and Y are as hereinbefore defined with a compound of formula III,

$L^1$—$(CH_2)_n$—B    III wherein $L^1$ represents a suitable leaving group (e.g. chloro, bromo, iodo, mesylate, triflate or arylsulfonate) and n and B are as hereinbefore defined, for example between 0 and 100° C. in the presence of a suitable base (e.g. potassium carbonate or triethylamine) and an appropriate solvent (e.g. acetonitrile, tetrahydrofuran or dimethylformamide);

(b) reaction of a compound of formula IV,

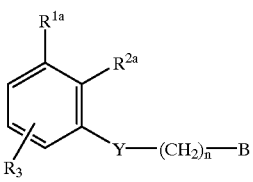

IV wherein one of $R^{1a}$ and $R^{2a}$ represents ZH and the other represents $R^4$, and Z, $R^3$, $R^4$, Y, n and B are as hereinbefore defined with a compound of formula V,

$L^2$—$SO_2$—Ar    V wherein $L^2$ is a suitable leaving group (e.g. chloro) and $Ar^1$ is as hereinbefore defined, under conditions which are well known to those skilled in the art, for example in the presence of a suitable base (e.g. pyridine or sodium bicarbonate) and, if appropriate, a suitable organic solvent;

(c) for compounds of formula I in which Y represents O or S, reaction of a compound of formula VI,

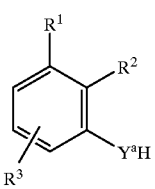

VI wherein $Y^a$ represents O or S and $R^1$, $R^2$ and $R^3$ are as hereinbefore defined with a compound of formula VII,

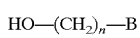

HO—$(CH_2)_n$—B    VII wherein n and B are as hereinbefore defined, for example at or below room temperature in the presence of an appropriate coupling system (e.g. diethylazodicarboxylate and triphenylphosphine) and a suitable organic solvent (e.g. tetrahydrofuran);

(d) for compounds of formula I wherein B represents a structural fragment of formula Ib or Id, reaction of a compound of formula VIII,

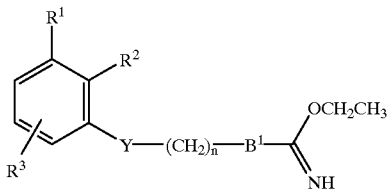
VIII wherein $B^1$ represents 1,4-phenylene or 1,4-cyclohexylene and $R^1$, $R^2$, $R^3$, Y and n are as hereinbefore defined with ammonia gas for example at room temperature in the presence of a suitable organic solvent (e.g. methanol or ethanol);

(e) for compounds of formula I wherein B represents a structural fragment of formula Ib or Id, reduction of a compound of formula IX,

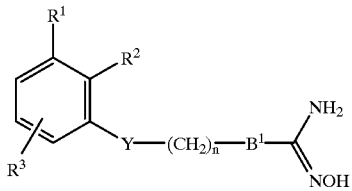
IX wherein $R^1$, $R^2$, $R^3$, Y, n and $B^1$ are as hereinbefore defined in the presence of a suitable reducing agent (for example by catalytic hydrogenation in the presence of e.g. Pd/C or $TiCl_3$) and an appropriate organic solvent;

(f) for compounds of formula I wherein B represents a structural fragment of formula Ib or Id, reaction of a compound of formula X,

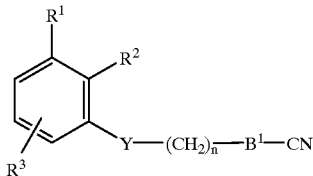
X wherein $R^1$, $R^2$, $R^3$, Y, n and $B^1$ are as hereinbefore defined with ammonium chloride, for example under reflux in the presence of a suitable catalyst (e.g. trimethyl aluminium) and an appropriate organic solvent (e.g. toluene);

(g) for compounds of formula I wherein Y represents S(O) or $S(O)_2$, oxidation of a corresponding compound of formula I wherein Y represents S in the presence of an appropriate quantity of a suitable oxidising agent (e.g. m-chloroperbenzoic acid or sodium periodate) and an appropriate organic solvent;

(h) for compounds of formula I wherein Z represents $N(R^5)$ and $R^5$ represents optionally substituted $C_{1-6}$alkyl, phenyl or $C_{1-3}$alkylphenyl, reaction of a corresponding compound of formula I wherein Z represents NH with a compound of formula XI, $$L^2-R^{5a} \qquad XI$$

wherein $R^{5a}$ represents optionally substituted $C_{1-6}$alkyl, phenyl or $C_{1-3}$alkylphenyl and $L^2$ is as hereinbefore defined, for example in the presence of suitable base (e.g. sodium hydride or potassium carbonate) and an appropriate organic solvent (e.g. DMF);

(i) for compounds of formula I wherein Z represents $N(R^5)$ and $R^5$ represents $C_{1-6}$alkyl, phenyl or $C_{1-3}$alkylphenyl, all of which are substituted and/or terminated by $C(O)N(R^{10})R^{11}$, reaction of a corresponding compound of formula I wherein $R^5$ represents $C_{1-6}$alkyl, phenyl or $C_{1-3}$alkylphenyl, all of which are substituted and/or terminated, by $C(O)OR^9$, wherein $R^9$ is as hereinbefore defined, with a compound of formula XII, $$HN(R^{10})R^{11} \qquad XII$$

wherein $R^{10}$ and $R^{11}$ are as hereinbefore defined, for example (in the case where $R^9$ represents H) in the presence of suitable a coupling system (e.g. DCC/HOBt or EDC/HOBt) and an appropriate organic solvent (e.g. DMF or acetonitrile); or (in the case where $R^9$ represents $C_{1-4}$alkyl) at room temperature in the presence of an appropriate organic solvent (e.g. MeOH or acetonitrile);

(j) for compounds of formula I wherein Z represents $N(R^5)$ and $R^5$ represents $C_{1-6}$alkyl, phenyl or $C_{1-3}$alkylphenyl, all of which are substituted and/or terminated by C(O)OH, hydrolysis of a corresponding compound of formula I wherein $R^5$ represents $C_{1-6}$alkyl, phenyl or $C_{1-3}$alkylphenyl, all of which are substituted and/or terminated by $C(O)OR^9$ and $R^9$ represents $C_{1-4}$alkyl under conditions which are well known to those skilled in the art; or (k) for compounds of formula I wherein Z represents $N(R^5)$ and $R^5$ represents $(CH_2)_2C(O)OR^9$ and $R^9$ is as hereinbefore defined, reaction of a corresponding compound of formula I wherein $R^5$ represents H with a compound of formula XIII, $$CH_2=CH-C(O)OR^9 \qquad XIII$$

wherein $R^9$ is as hereinbefore defined, for example by refluxing in the presence of a catalytic amount of an appropriate organic acid (e.g. acetic acid).

Compounds of formulae II and VI are commercially available, are known in the literature or are available using known techniques. For example compounds of formulae II and VI may be prepared by reaction of a compound of formula XIV,

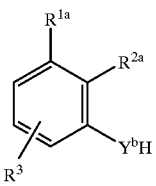
XIV wherein $Y^b$ represents Y or $Y^a$ as appropriate and $R^{1a}$, $R^{2a}$ and $R^3$ are as hereinbefore defined with a compound of formula V as hereinbefore defined, for example under similar conditions to those described hereinbefore for synthesis of compounds of formula I (process (b)).

Compounds of formulae III and VII are commercially available, are known in the literature or are available using known techniques. For example compounds of formulae III and VII wherein B represents a structural fragment of formula Ib or Id may be prepared by reaction of a corresponding compound of formula XV,

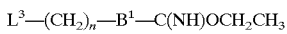     XV wherein $L^3$ represents $L^1$ or OH as appropriate and n and $B^1$ are as hereinbefore defined with ammonia gas for example under similar conditions to those described hereinbefore for synthesis of compounds of formula I (process (d)).

Compounds of formula IV may be prepared by reaction of a compound of formula XIV wherein $Y^b$ represents Y and Y is as hereinbefore defined with a compound of formula III as hereinbefore defined, for example under similar conditions to those described hereinbefore for synthesis of compounds of formula I (process (a)).

Compounds of formula IV in which Y represents O or S may alternatively be prepared by reaction of a compound of formula XIV wherein $Y_b$ represents $Y^a$ and $Y^a$ is as hereinbefore defined with a compound of formula VII, for example under similar conditions to those described hereinbefore for synthesis of compounds of formula I (process (c)).

Compounds of formula IV in which B represents a structural fragment of formula Ib or Id may alternatively be prepared by reaction of a compound of formula XVI,

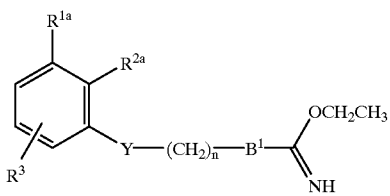     XVI wherein $R^{1a}$, $R^{2a}$, $R^3$, Y, n and $B^1$ are as hereinbefore defined with ammonia gas for example under similar conditions to those described hereinbefore for synthesis of compounds of formula I (process (d)).

Compounds of formula IV in which B represents a structural fragment of formula Ib or Id may alternatively be prepared by reduction of a compound of formula XVII,

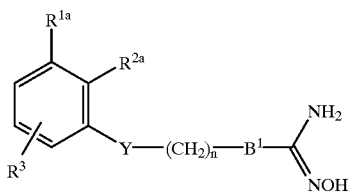     XVII wherein $R^{1a}$, $R^{2a}$, $R^3$, Y, n and $B^1$ are as hereinbefore defined, under similar conditions to those described hereinbefore for synthesis of compounds of formula I (process (e)).

Compounds of formulae VIII, XV and XVI may be prepared by reaction of a corresponding cyanobenzene of formula X as hereinbefore defined (for a compound of formula VIII), a corresponding cyanobenzene of formula XVIII,

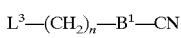     XVIII wherein $L^3$, n and $B^1$ are as hereinbefore defined (for a compound of formula XV), or a corresponding cyanobenzene of formula XIX,

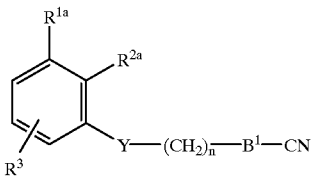     XIX wherein $R^{1a}$, $R^{2a}$, $R^3$, Y, n and $B^1$ are as hereinbefore defined (for a compound of formula XVI), with HCl(g) and ethanol, for example at or below room temperature (e.g. 0° C.).

Compounds of formula IX and XVII may be prepared by reaction of a compound of formula X or XIX as hereinbefore defined (as appropriate) with hydroxylamine, for example at or around 40° C. in the presence of a suitable base (e.g. triethylamine) and an appropriate organic solvent (e.g. ethanol).

Compounds of formula X may be prepared by reaction of a compound of formula XIX as hereinbefore defined with a compound of formula V as hereinbefore defined for example under similar conditions to those described hereinbefore for synthesis of compounds of formulae I (process (b)), II and VI.

Compounds of formula X may alternatively be prepared by reaction of a compound of formula II as hereinbefore defined with a compound of formula XX

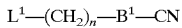     XX wherein $L^1$, n and $B^1$ are as hereinbefore defined, for example under similar conditions to those described hereinbefore for synthesis of compounds of formula I (process (a)).

Compounds of formula X wherein Y represent O or S may alternatively be prepared by reaction of a compound of formula VI as hereinbefore defined with a compound of formula XXI

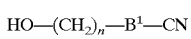     XXI wherein n and $B^1$ are as hereinbefore defined, for example under similar conditions to those described hereinbefore for synthesis of compounds of formula I (process (c)).

Compounds of formula XIX may be prepared by reaction of a compound of formula XIV wherein $Y^b$ represents Y and Y is as hereinbefore defined with a compound of formula XX as hereinbefore defined, for example under similar conditions to those described hereinbefore for synthesis of compounds of formula I (process (a)).

Compounds of formula XIX wherein Y represents O or S may be prepared by reaction of a compound of formula XIV wherein $Y^b$ represents $Y^a$ and $Y^a$ is as hereinbefore defined with a compound of formula XXI as hereinbefore defined, for example under similar conditions to those described hereinbefore for synthesis of compounds of formula I (process (c)).

Compounds of formulae II, IV, VI, VIII, IX, X, XIV, XVI, XVII and XIX wherein Z represents $N(R^5)$ and $R^5$ represents optionally substituted $C_{1-6}$alkyl, phenyl or $C_{1-3}$alkylphenyl, may be prepared by reaction of a corresponding compound of formula II, IV, VI, VIII, IX, X, XIV, XVI, XVII or XIX (as appropriate) wherein Z represents NH with a compound of formula XI as hereinbefore defined, for example under similar conditions to those described hereinbefore for synthesis of compounds of formula I (process (h)).

Compounds of formulae II, IV, VI, VIII, IX, X, XIV, XVI, XVII and XIX wherein Z represents $N(R^5)$ and $R^5$ represents $C_{1-6}$alkyl, phenyl or $C_{1-3}$alkylphenyl substituted and/or terminated, in all three cases, by $C(O)N(R^{10})R^{11}$ may alternatively be prepared by reaction of a corresponding compound of formula II, IV, VI, VIII, IX, X, XIV, XVI, XVII or XIX (as appropriate) wherein $R^5$ represents $C_{1-6}$alkyl, phenyl or $C_{1-3}$alkylphenyl substituted and/or terminated, in all three cases, by $C(O)OR^9$, wherein $R^9$ is as hereinbefore defined, with a compound of formula XII as hereinbefore defined, for example under similar conditions to those described hereinbefore for synthesis of compounds of formula I (process (i)).

Compounds of formulae II, IV, VI, VIII, IX, X, XIV, XVI, XVII and XIX wherein Z represents $N(R^5)$ and $R^5$ represents $C_{1-6}$alkyl, phenyl or $C_{1-3}$ alkylphenyl substituted and/or terminated, in all three cases, by C(O)OH may alternatively be prepared by hydrolysis of a corresponding compound of formula II, IV, VI, VIII, IX, X, XIV, XVI, XVII or XIX (as appropriate) wherein $R^5$ represents $C_{1-6}$alkyl, phenyl or $C_{1-3}$alkylphenyl substituted and/or terminated, in all three cases, by $C(O)OR^9$ and $R^9$ represents $C_{1-4}$alkyl under conditions which are well known to those skilled in the art.

Compounds of formulae II, IV, VI, VIII, IX, X, XIV, XVI, XVII and XIX wherein Z represents $N(R^5)$ and $R^5$ represents $(CH_2)_2C(O)OR^9$ and $R^9$ is as hereinbefore defined, may alternatively be prepared by reaction of a corresponding compound of formula II, IV, VI, VIII, IX, X, XIV, XVI, XVII or XIX (as appropriate) wherein $R^5$ represents H with a compound of formula XIII as hereinbefore defined, for example under similar conditions to those described hereinbefore for synthesis of compounds of formula I (process (k)).

Compounds of formulae V, XI, XII, XIII, XIV, XVIII, XX and XXI are either commercially available, are well known in the literature, or are available using known techniques. For example compounds of formula XIV wherein $R^{1a}$ and/or $R^{2a}$ represent $NH_2$ may be prepared by reduction of the corresponding nitrobenzene under conditions which are well known to those skilled in the art. Similarly, compounds of formula XIV wherein $R^{1a}$ and/or $R^{2a}$ represent OH may be prepared by hydrolysis of a corresponding alkoxybenzene under conditions which are well known to those skilled in the art. Compounds of formulae IV, XVI, XVII and XIX wherein $R^{1a}$ and/or $R^{2a}$ represent $NH_2$ or OH may also be prepared from the corresponding nitrobenzene or alkoxybenzene (as appropriate) in accordance with these techniques.

Substituents on the aromatic and/or non-aromatic, carbocyclic and/or heterocyclic ring(s) in compounds of formulae I, II, IV, V, VI, VIII, IX, X, XI, XII, XIV, XVI, XVII and XIX may be interconverted by techniques well known to those skilled in the art.

The compounds of the invention may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino, amidino, guanidino and carboxylic acid. Suitable protecting groups for hydroxy include trialkylsilyl and diarylalkylsilyl groups (e.g. t-butyldimethylsilyl, t-butyldiphenylsilyl or trimethylsilyl) and tetrahydropyranyl. Suitable protecting groups for hydroxy groups, which groups are attached to adjacent carbon atoms include O,O'-isopropylidene. Suitable protecting groups for amino, amidino and guanidino include t-butyloxycarbonyl or benzyloxycarbonyl. Amidino and guanidino nitrogens may be either mono- or diprotected. Suitable protecting groups for carboxylic acid include $C_{1-6}$alkyl or benzyl esters.

The protection and deprotection of functional groups may take place before or after a reaction step.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

It will also be appreciated by those skilled in the art that, "protected derivatives" of compounds of formula I may be formed prior to a final deprotection step. Although they may not possess pharmacological activity as such, certain "protected derivatives" of compounds of formula I may be administered parenterally or orally and thereafter metabolised in the body to form compounds of the invention which are pharmacologically active. Such derivatives may therefore be described as "prodrugs". All prodrugs of compounds of formula I are included within the scope of the invention.

Medical and pharmaceutical Use

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent inhibitors of thrombin for example as demonstrated in the tests described below.

The compounds of the invention are thus expected to be useful in those conditions where inhibition of thrombin is required.

The compounds of the invention are thus indicated in the treatment or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (eg in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

Biological Tests

Test A

Determination of Thrombin Clotting Time (TT)

Human thrombin (T 6769, Sigma Chem. Co) in buffer solution, pH 7.4, 100 μl, and inhibitor solution, 100 μl, were incubated for one minute. Pooled normal citrated human plasma, 100 μl, was then added and the clotting time measured in an automatic device (KC 10, Amelung).

The clotting time in seconds was plotted against the inhibitor concentration, and the $IC_{50}TT$ was determined by interpolation.

$IC_{50}TT$ is the concentration of inhibitor in the test that doubles the thrombin clotting time for human plasma.

Test B

Determinaton of Thrombin Inhibition with a Chromogenic Robotic Assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 1 mmol/L, were diluted serially 1:3 (24+48 μL) with DMSO to obtain ten different concentrations, which were analysed as samples in the assay. 2 μL of test sample was diluted with 124 μL assay buffer, 12 μL of chromogenic substrate solution (S-2366, Chromogenix, Mölndal, Sweden) in assay buffer and finally 12 μL of α-thrombin solution, (Human α-thrombin, Sigma Chemical Co.) both in assay buffer, were added, and the samples mixed. The final assay concentrations were: test substance 0.00068–13.3 μmol/L, S-2366 0.30 mmol/L, α-thrombin 0.020 NIHU/mL. The linear absorbance increment during 40 minutes incubation at 37° C., was used for calculation of percentage inhibition for the test samples, as compared to blanks without inhibitor. The $IC_{50}$-robotic value, corresponding to the inhibitor concentration which caused 50% inhibition of the thrombin activity, was calculated from a log dose vs. % inhibition curve.

Test C

Determinaton of the Inhibition Constant $K_i$ for Human Thrombin $K_i$-determinations were made using a chromogenic substrate method, performed at 37° C. on a Cobas Bio centrifugal analyser (Roche, Basel, Switzerland). Residual enzyme activity after incubation of human α-thrombin with various concentrations of test compound was determined at three different substrate concentrations, and was measured as the change in optical absorbance at 405 nm.

Test compound solutions (100 µL; normally in buffer or saline containing BSA 10 g/L) were mixed with 200 µL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 µL sample, together with 20 µL of water, was added to 320 µL of the substrate S-2238 (Chromogenix AB, Mölndal, Sweden) in assay buffer, and the absorbance change (ΔA/min) was monitored. The final concentrations of S-2238 were 16, 24 and 50 µmol/L and of thrombin 0.125 NIH U/ml.

The steady state reaction rate was used to construct Dixon plots, i.e. diagrams of inhibitor concentration vs. $1/(\Delta A/min)$. For reversible, competitive inhibitors, the data points for the different substrate concentrations typically form straight lines which intercept at $x=-K_i$.

Test D

Determination of Activated Partial Thromboplastin Time (APTT)

APTT was determined in pooled normal human citrated plasma with the reagent PTT Automated 5 manufactured by Stago. The inhibitors were added to the plasma (10 µL inhibitor solution to 90 µL plasma) followed by the reagent and calcium chloride solution and APTT was determined in the mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in human plasma that doubled the Activated Partial Thromboplastin Time.

Test E

Determination of Thrombin Time ex vivo

The inhibition of thrombin after oral or parenteral administration of the compounds of the invention were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L) and 9 parts of blood. The tubes were centrifuged to obtain platelet poor plasma. The plasma was used for determination of thrombin time as described above.

The citrated rat plasma, 100 µL, was diluted with a saline solution, 0.9%, 100 µL, and plasma coagulation was started by the addition of human thrombin (T 6769, Sigma Chem Co, USA) in a buffer solution, pH 7.4, 100 µL. The clotting time was measured in an automatic device (KC 10, Amelumg, Germany).

The invention is illustrated by way of the following examples

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS). $^1$H NMR and $^{13}$C NMR measurements were performed on BRUKER ACP 300 and Varian UNITY plus 400, 500 and 600 spectrometers, operating at $^1$H frequencies of 300.13, 399.96, 499.82 and 599.94 MHz respectively, and at $^{13}$C frequencies of 75.46, 100.58, 125.69 and 150.88 MHz respectively. Flash chromatography was carried out on silica gel (230–400 mesh). Preparative HPLC was performed on reverse phase columns (250 mm, 20 or 50 mm; 5 to 7 µM phase Chromasil C8) with flow rates of 10 to 50 mL/min using a UV detector (270 to 280 nm).

Example 1

N-{3-[2-(4-Aminoiminomethylphenyl)ethoxy]phenyl}benzenesulfonamide×HCl (i) t-Butyloxycarbonylamino-3-hydroxybenzene Amino-3-hydroxybenzene (5.46 g; 50 mmol) was dissolved in THF (50 mL) and di-t-butyl dicarbonate (12.0 g; 55 mmol) was added at room temperature. The solution was heated for 2 hours at 60° C., the solvent was evaporated and the residue was dissolved in EtOAc (150 mL). The EtOAc-phase was washed with 2×20 mL of 1M KHSO$_4$, 1×20 mL water, 1×20 mL brine and then dried (MgSO$_4$). The solvent was evaporated to give 11.74 g of a colourless oil which was crystallised from CH$_2$Cl$_2$:MeOH:light petroleum to give 9.1 g (87%) of the sub-title compound as white crystals.

$^1$H-NMR (400 MHz; CDCl$_3$): δ7.10–7.15 (bs, 1H), 7.11 (t, 1H), 6.72 (dd, 1H), 6.53 (dd, 1H), 6.50 (bs, 1H), 5.57 (apparent bs, 1H), 1.52 (s, 9H) $^{13}$C-NMR (100 MHz; CDCl$_3$): δ156.4, 152.8, 139.4, 129.9, 110.7, 110.2, 105.9, 80.8, 28.3

(ii) t-Butyloxycarbonylamino-3-[2-(4-cyanophenyl)ethoxy]benzene

To a solution of t-butyloxycarbonylamino-3-hydroxybenzene (418.5 mg; 2 mmol; from step (i) above), triphenylphosphine (629.5 mg; 2.4 mmol) and 2-(4-cyanophenyl)ethanol (353.2 mg; 2.4 mmol) in THF (50 mL), under an atmosphere of nitrogen, was added diethylazodicarboxylate (518 mg; 3 mmol) and the mixture was stirred for one week. Ice cold water was added and the THF was removed by evaporation. The remaining water phase was extracted three times with EtOAc. The combined organic phase was washed twice with 0.2 M NaOH, once with brine, and then dried (Na$_2$SO$_4$). Evaporation followed by flash chromatography using a stepwise gradient of toluene:EtOAc (100:0, 90:10, 80:20 and 60:40) gave 300 mg (44%) of the sub-title compound.

$^1$H-NMR (300 MHz; CDCl$_3$): δ7.57 (d, 2H), 7.37 (d, 2H), 7.21 (bs, 1H), 7.14 (t, 1H), 6.76 (dd, 1H), 6.67 (bs, 1H, NH), 6.54 (dd, 1H), 4.16 (t, 2H), 3.10 (t, 2H), 1.50 (s, 9H)

$^{13}$C-NMR (75 MHz; CDCl$_3$): δ159.05, 152.57, 144.17, 139.65, 132.05, 129.74, 129.52, 118.84, 110.82, 110.14, 109.10, 104.52, 80.41, 67.43, 35.65, 28.20

(iii) Amino-3-[2-(4-cyanophenyl)ethoxy]benzene×HCl t-Butyloxycarbonylamino-3-[2-(4-cyanophenyl)ethoxy]benzene (300 mg; 0.89 mmol; from step (ii) above) was dissolved in EtOAc, pre-saturated with HCl(g), at room temperature and stirred for 1 hour. The solvent and the excess HCl(g) was evaporated to give 231 mg (94%) of the sub-title compound.

¹H-NMR (400 MHz; CD₃OD): δ7.66 (d, 2H), 7.50 (d, 2H), 7.40 (t, 1H), 7.01 (bd, 1H), 6.90 (bd, 1H), 6.85 (bs, 1H), 4.28 (t, 2H), 3.18 (t, 2H)

(iv) N-{3-[2-(4-Cyanophenyl)ethoxy]phenyl}benzenesulfonamide

To a cold (ice:water temperature) solution of amino-3-[2-(4-cyanophenyl)ethoxy]benzene×HCl (231 mg; 0.84 mmol; from step (iii) above) in pyridine (2 mL) was added benzenesulfonyl chloride (119 μL; 0.93 mmol) and the mixture was allowed to reach room temperature and stirred for three days. The pyridine was removed by evaporation and the residue was partitioned between water and EtOAc. The phases was separated and the water phase was extracted twice with EtOAc and the combined organic phase was washed once with 1M KHSO₄, brine and dried (Na₂SO₄). The solvent was evaporated and the residue was subjected to purification by flash chromatography using a stepwise gradient of toluene:EtOAc (100:0, 90:10, 80:20, 60:40 and 40:60) as eluent to give 277 mg (87%) of the sub-title compound.

LC-MS 377 (M−1)⁻

¹H-NMR (400 MHz; CDCl₃): δ7.82 (d, 2H), 7.75 (bs, 1H, NH), 7.56 (d, 2H), 7.47–7.53 (m, 1H), 7.40 (t, 2H), 7.35 (d, 2H), 7.07 (t, 1H), 6.75 (bt, 1H), 6.65–6.70 (m, 1H), 6.59 (dd, 1H), 4.10 (t, 2H), 3.07 (t, 2H)

(v) N-{3-[2-(4-Ethoxyiminomethylphenyl)ethoxy]phenyl}benzenesulfonamide×HCl

A gentle stream of HCl(g) was passed into a cooled (0° C.) solution of N-{3-[2-(4-cyanophenyl)ethoxy]phenyl}benzenesulfonamide (257 mg; 0.68 mmol; from step (iv) above) in absolute EtOH (10 mL) until the temperature was stabilized at 0° C. The mixture was allowed to reach room temperature and stirred at this temperature for 24 hours. The solvent was evaporated to give the sub-title compound in a quantitative yield.

¹H-NMR (600 MHz; CD₃OD): δ7.96 (d, 2H), 7.70–7.73 (m, 2H), 7.55 (d, 2H), 7.50–7.54 (m, 1H), 7.43 (t, 2H), 7.03 (t, 1H), 6.67 (t, 1H), 6.56 (dd, 2H), 4.60 (q, 2H), 4.15 (t, 2H), 3.14 (t, 2H), 1.59 (t, 3H)

(vi) N-{3-[2-(4-Aminoiminomethylphenyl)ethoxy]phenyl}benzene-sulfonamide×HCl

N-{3-[2-(4-Ethoxyiminomethylphenyl)ethoxy]phenyl}benzenesulfonamide×HCl (313 mg; 0.68 mmol; from step (v) above) was dissolved in methanol, saturated with ammonia gas and stirred at room temperature for three days. A precipitate had formed and, after addition of 0.5 mL Et₂O, the mixture was place in a freezer overnight. The precipitate was collected by filtration and the filter-cake was washed with cool MeOH (1 mL) and Et₂O (3 mL). The crystals were dried and added to MeOH (8 mL) to form a slurry. MeOH saturated with HCl(g) was added until the solution became clear and the volume was concentrated to give 2–3 mL. Addition of Et₂O (20 mL) caused a precipitate to form which was filtered and dried under vacuum to yield 169 mg (57%) of the title compound.

FAB-MS 396 (M+1)⁺

¹H-NMR (400 MHz; CD₃OD): δ9.20 (bs, 1H, NH), 8.71 (bs, 1H, NH), 7.72–7.77 (m, 4H), 7.51–7.57 (m, 3H), 7.42–7.49 (m, 2H), 7.05 (t, 1H), 670 (t, 1H), 6.56–6.62 (m, 2H), 4.16 (t, 2H), 3.14 (t, 2H)

¹³C-NMR (100 MHz; CDCl₃): δ160.64, 147.36, 147.02, 141.04, 140.14, 133.89, 131.14, 130.93, 130.01, 128.99, 128.16, 114.49, 111.83, 108.52, 69.00, 36.38

Example 2

Benzenesulfoniacid-{3-[2-(4-aminoiminomethylphenyl)ethoxy]-5-methyl}-phenyl ester×HCl (i) Benzenesulfonic acid-(3-hydroxy-5-methyl)phenyl ester Benzenesulfonyl chloride (6.36 g; 36 mmol) was added to a well stirred mixture of 3,5-dihydroxytoluene×H₂O (4.26 g; 30 mmol), saturated aqueous NaHCO₃ (70 mL) and Et₂O (50 mL) and the mixture was stirred at room temperature for 19 hours. Et₂O (50 mL) was added and the organic layer was separated, collected and evaporated to give 7.05 g of a powder. The crude material was recrystallized from EtOAc:heptane (30 mL:300 mL) to give 4.36 g (55%) of the sub-title compound.

FAB-MS 265 (M+1)⁺

¹H-NMR (400 MHz; CDCl₃): δ7.86 (d, 2H), 7.67 (tt, 1H), 7.53 (t, 2H), 6.54 (bs, 1H), 6.38 (bs, 1H), 6.31 (t, 1H), 5.02 (s, 1H, OH), 2.21 (s, 3H)

(ii) Benzenesulfonic acid-{3-[2-(4-cyanophenyl)ethoxy]-5-methyl}phenyl ester

Diethylazodicarboxylate (1.74 g; 10 mmol) was added, over 5 minutes, to a stirred solution of triphenylphosphine (2.62 g; 10 mmol), 2-(4-cyanophenyl)ethanol (1.47 g; 10 mmol) and benzenesulfonic acid-(3-hydroxy-5-methyl)-phenyl ester (2.64 g; 10 mmol; from step (i) above) in THF (25 mL) at room temperature. The stirring was continued for an additional 17 hours, the THF was evaporated and the residue was dissolved in EtOAc (150 mL). The organic phase was washed with 2×25 mL of 1M NaOH, 1×25 mL of 1M KHSO₄, 1×10 mL of brine and dried (MgSO₄). The solvent was evaporated to give 9.09 g of an oil. Purification by flash chromatography using a stepwise gradient of toluene:EtOAc (100:0, 20:1 and 10:1) gave 2.79 g (71%) of the sub-title compound as a white powder.

FAB-MS 394 (M+1)⁺

¹H-NMR (400 MHz; CDCl₃): δ7.85 (apparent dd, 2H), 7.66 (tt, 1H), 7.60 (apparent d, 2H), 7.50–7.55 (m, 2H), 7.35 (d, 2H), 6.57 (bs, 1H), 6.35–6.38 (m, 2H), 4.07 (t, 2H), 3.08 (t, 2H), 2.21 (s, 3H)

(iii) Benzenesulfonic acid-{3-[2-(4-ethoxyiminomethylphenyl)ethoxy}-5-methyl}phenyl ester×HCl EtOH (25 mL) was cooled to 5° C. and a gentle stream of HCl(g) was bubbled through until saturation. Benzenesulfonic acid-{3-[2-(4-cyanophenyl)ethoxy]-5-methyl}phenyl ester (590 mg; 1.5 mmol; from step (ii) above) was added to the cold solution in one portion and the mixture was allowed to reach room temperature and stirred over night. The solvent and excess HCl(g) was evaporated to give the sub-title compound in a quantitative yield.

¹H-NMR (400 MHz; CD₃OD): δ7.99 (apparent d, 2H), 7.81 (apparent d, 2H), 7.72 (dt, 1H), 7.53–7.62 (m, 4H), 6.63 (bs, 1H), 6.34 (bs, 1H), 6.30 (apparent t, 1H), 4.63 (q, 2H), 4.13 (t, 2H), 3.14.(t, 2H), 2.18 (s, 3H), 1.61 (t, 3H)

(iv) Benzenesulfonic acid-{3-[2-(4-aminoiminomethylphenyl)ethoxy ]-5-methyl}phenyl ester×HCl Benzenesulfonic acid-{3-[2-(4-ethoxyiminomethylphenyl)ethoxy]-5-methyl}phenyl ester×

HCl (1.5 mmol; from step (iii) above) was dissolved in MeOH pre-saturated by ammonia and the reaction was stirred at room temperature for 24 hours. The solvent and excess ammonia were evaporated and the residue was dissolved in MeOH (5 mL). 6 mL of 1.77 M HCl(g) in MeOH was added and the solution was concentrated to about 3 mL. Et$_2$O (60 mL) was added to precipitate the hydrochloride salt of the title compound. The volume was reduced to 45 mL and the mixture was placed in a freezer for two days. Collection of the precipitate by filtration followed by drying under vacuum gave 575 mg (86%; calculated from the nitrile above) of the pure title compound as a white powder.

FAB-MS 411 (M +1)$^+$ $^1$H-NMR (400 MHz; CD$_3$OD): δ7.79–7.83 (m, 2H), 7.70–7.77 (m, 3H), 7.58 (apparent t, 2H), 7.52 (d, 2H), 6.63 (bs, 1H), 6.34 (bs, 1H), 6.29 (bs, 1H), 4.11 (t, 2H), 3.11 (t, 2H), 2.18 (s, 3H)

Example 3

N-{3-[2-(4-Aminoiminomethylphenyl)ethoxyl]phenyl}-2-chlorobenzenesulfonamide×HOAc (i) Nitro-3-[2-(4-cyanophenyl)ethoxy]benzene Triphenylphosphine (11.3 g; 43.1 mmol) and diethylazodicarboxylate (7.5 g; 43 mmol) were dissolved in THF (250 mL) under nitrogen at 0° C. After 5 minutes, 3-nitrophenol (5.00 g; 35.9 mmol) and 2-(4-cyanophenyl)ethanol (6.3 g; 43 mmol) were added. The cooling bath was removed and the mixture stirred for 2 days at room temperature. A new batch was prepared as above and the two were combined before work-up. Water was added and the THF was evaporated. The mixture was extracted with EtOAc, and the organic phase was washed with aqueous 0.2M NaOH and brine, dried (Na$_2$SO$_4$) and the solvent removed in vacuo. Purification by flash chromatography (SiO$_2$; toluene) and recrystallization from CH$_2$Cl$_2$:EtOH afforded 3.07 g (32%) of the sub-title compound.

$^1$H NMR (500 MHz; CDCl$_3$): δ7.82 (dd, 1H), 7.61–7.71 (several peaks, 4H), 7.41 (d, 2H), 7.19 (dd, 1H), 4.27 (t, 2H), 3.19 (t, 2H)

(ii) Amino-3-[2-(4-cyanophenyl)ethoxy]benzene

Nitro-3-[2-(4-cyanophenyl)ethoxy]benzene (3.0 g; 11.2 mmol; from step (i) above) and NH$_4$Cl (2.9 g; 55 mmol) were dissolved in a mixture of EtOH (40 mL) and H$_2$O (10 mL) and heated to reflux. Iron powder (3.0 g; 55 mmol) was added and heating was continued for 1 hour. The mixture was filtered, concentrated in vacuo and partitioned between water and CH$_2$Cl$_2$. After separation, the aqueous phase was extracted with CH$_2$Cl$_2$. The combined organic phases were dried (MgSO$_4$) and the solvent was evaporated. Purification by flash chromatography (SiO$_2$; toluene:EtOAc (9:1)) afforded 2.26 g (85%) of the sub-title compound.

LC-MS 239 (M+1)$^+$ $^1$H NMR (300 MHz; CDCl$_3$): δ7.59 (d, 2H), 7.39 (d, 2H), 7.05 (t, 1H), 6.32 (m, 2H), 6.24 (t, 1H), 4.15 (t, 2H), 3.12 (t, 2H), 2.0 (s, 2H)

(iii) N-{3-[2-(4-Cyanophenyl)ethoxy]phenyl}-2-chlorobenzenesulfonamide

Pyridine (0.255 mL; 3.15 mmol) was added to a stirred solution of amino-3-[2-(4-cyanophenyl)ethoxy]benzene (0.15 g; 0.629 mmol; from step (ii) above) and 2-chlorobenzenesulfonyl chloride (0.173 mL; 0.818 mmol) in CH$_2$Cl$_2$ (4 mL). After 45 minutes at room temperature the solvent was removed in vacuo. To remove traces of pyridine, EtOH was added and evaporated. The residue was partitioned between water and EtOAc. The organic layer was washed with 0.1M aqueous HCl and brine, dried (Na$_2$SO$_4$) and the solvent removed in vacuo. Purification by flash chromatography (SiO$_2$; toluene:EtOAc (1:0 to 9:1)) afforded 0.095 g (35%) of the sub-title compound.

$^1$H NMR (400 MHz; CD$_3$OD): δ8.02 (dd, 1H), 7.62 (d, 2H), 7.45–7.52 (several peaks, 2H), 7.32–7.40 (several peaks, 3H), 7.09 (m, 2H), 6.75 (t, 1H), 6.65 (dd, 1H), 6.59 (dd, 1H), 4.13 (t, 2H), 3.11 (t, 2H)

(iv) N-{3-[2-(4-Ethoxyiminomethylphenyl)ethoxy]phenyl}-2-chloro-benzenesulfonamide×HCl N-{3-[2-(4-Cyanophenyl)ethoxy]phenyl3}-2-chlorobenzenesulfonamide (0.070 g; 0.163 mmol; from step (iii) above) was added to a saturated solution of HCl(g) in EtOH (100 mL) and the solution stirred for 24 hours. Evaporation of the solvent afforded the sub-title compound in a quantitative yield.

LC-MS 459 (M+1)$^+$ (v) N-{3-[2-(4-Aminoiminomethylphenyl)ethoxy]phenyl}-2-chlorobenzene-sulfonamide×HOAc N-{3-[2-(4-Ethoxyiminomethylphenyl)ethoxy]phenyl}-2-chlorobenzene-sulfonamide×HCl (0.080 g, 0.16 mmol; from step (iv) above) was dissolved in MeOH (pre-saturated with NH$_3$(g)) and stirred at room temperature for 1 day. The solvent was evaporated and the residue purified by preparative HPLC (40% CH$_3$CN:0.1M NH$_4$OAc) to afford 0.020 g (25%) of the title compound.

LC-MS 430 (M+1)$^+$ $^1$H NMR (400 MHz; CD$_3$OD): δ8.02 (dd, 1H), 7.73 (d, 2H), 7.50–7.55 several peaks, 4H), 7.38 (m, 1H), 7.04 (t, 1H), 6.70 (t, 1H), 6.65 (m, 1H), 6.59 (m, 1H), 4.14 (t, 2H), 3.13 (t, 2H), 1.90 (s, 3H)

Example 4

N-{3-[2-(4-Aminoiminomethylphenyl)ethoxy]phenyl}-2-cyanobenzene-sulfonamide×HCl (i) 3-[2-(4-Ethoxyiminomethylphenyl)ethoxy]nitrobenzene×HCl A gentle stream of HCl(g) was passed into a cooled (NaCl:ice) suspension of nitro-3-[2-(4-cyanophenyl)ethoxy]benzene (2.80 g; 10.4 mmol; from Example 3(i) above) in EtOH (200 mL) until the temperature was stabilized at 0° C. After 3.5 hours stirring the temperature was allowed to rise to ambient and the stirring was continued for 24 hours. Evaporation of the solvent in vacuo gave the sub-title compound in a quantitative yield.

$^1$H NMR (400 MHz; CD$_3$OD): δ8.00 (d, 2H), 7.80 (ddd, 1H), 7.70 (t, 1H), 7.63 (d, 2H), 7.48 (t, 1H), 7.30 (ddd, 1H), 4.62 (q, 2H), 4.38 (t, 2H), 3.28 (t, 2H), 1.60 (t, 3H)

(ii) 3-[2-(4-Aminoiminomethylphenyl)ethoxy]nitrobenzene×HCl

3-[2-(4-Ethoxyiminomethylphenyl)ethoxy]nitrobenzene×HCl (3.6 g; 10.4 mmol; from step (i) above) was dissolved in MeOH, pre-saturated with NH$_3$(g), and stirred at room temperature for 3 days. Addition of Et$_2$O (150 mL) failed to give any precipitate. Evaporation of the solvent in vacuo afforded the sub-title compound in a quantitative yield.

LC-MS 286 (M+1)$^+$

(iii) 3-[2-(4-Amino{t-butoxycarbonylimino}methylphenyl)ethoxy]nitrobenzene

3-[2-(4-Aminoiminomethylphenyl)ethoxy]nitrobenzene×HCl (3.49 g; 10.8 mmol; from step (ii) above) was dissolved in THF (20 mL) and water (10 mL). Aqueous NaOH (10 mL; 1M; 10 mmol) and di-t-butylcarbonate (2.24 g; 10.3 mmol) were added and the solution stirred at room temperature for 1 hour. THF was removed in vacuo and the aqueous residue was extracted twice with EtOAc. The combined organic phases were filtered and the solvent evaporated. Purification by flash chromatography (SiO$_2$; CH$_2$Cl$_2$) resulted in partial decomposition of the product. The most pure fractions were combined and recrystallized from CH$_2$Cl$_2$:Et$_2$O to give 2.02 g (51%) of the sub-title compound.

LC-MS 386 (M+1)$^+$

(iv) Amino-3-[2-(4-amino{t-butoxycarbonylimino}methylphenyl)ethoxy]-benzene A suspension of 3-[2-(4-amino{t-butoxycarbonylimino}methylphenyl)-ethoxy]nitrobenzene (1.47 g; 3.81 mmol; from step (iii) above) and Pd (0.236 g; 5% on charcoal) in EtOH (75 mL) was stirred under H$_2$(g) (1 atm.) for 25 minutes. After filtration through Celite the solvent was evaporated. The residue was purified by preparative HPLC (60% CH$_3$CN/aq:0.1M NH$_4$OAc) to afford the sub-title compound. Yield: 1.02 g (75%).

20 FAB-MS 356 (M+1)$^+$ $^1$H NMR (300 MHz; CDCl$_3$): δ7.80 (d, 2H), 7.35 (d, 2H), 7.05 (t, 1H), 6.25–6.35 (m, 2H), 6.20 (t, 1H), 4.15 (t, 2H), 3.65 (bs, 2H), 3.12 (t, 2H), 1.55 (s, 9H)

(v) N-{3-[2-(4-Aminoiminomethylphenyl)ethoxy]phenyl}-2-cyanobenzene-sulfonamide×HCl Prepared using a Vac-Master in accordance with the following procedure.: Two solutions, one of amino-3-[2-(4-amino {t-butoxycarbonylimino}-methylphenyl)ethoxy]benzene (0.0804M; from step (iv) above) and 4-dimethylaminopyridine (0.1046M) in CH$_3$CN, and one of 2-cyanophenylsulfonyl chloride (0.124M) in CH$_3$CN were prepared. The solutions (0.700 mL of the first and 0.540 mL of the second) were mixed and left for 6 hours without stirring. The mixture was then filtered through a short plug of silica gel (0.50 g), that was washed with CH$_3$CN (2×1 mL). The solvent was removed by a stream of nitrogen gas. The residue was treated with EtOAc, pre-saturated with HCl(g), (3 mL) overnight and the solvent was removed by a stream of nitrogen gas affording the title compound. To estimate the yield, the purity was determined by reversed phase LC (Chromasil C8, 0–100% CH$_3$CN/aq:0.1M NH$_4$OAc) with UV-detection (254 nm). Yield: 48% (LC).

LC-MS 421 (M+1)$^+$, 419 (M−1)$^−$

Example 5

N-{3-[2-(4-Aminoiminomethylphenyl)ethoxy]phenyl}-2-fluorobenzene-sulfonamide×HCl Prepared according to the procedure described in Example 4(v) above, using 2-fluorobenzenesulfonyl chloride instead of 2-cyanophenylsulfonyl chloride. Yield: 80% (LC).

LC-MS 414 (M+1)$^+$, 412 (M−1)$^−$

Example 6

N-{3-[2-(4-Aminoiminomethylphenyl)ethoxy]phenyl}-2-(trifluoromethoxy)-benzenesulfonamide×HCl Prepared according to the procedure described in Example 4(v) above, using 2-(trifluoromethoxy)benzenesulfonyl chloride instead of 2-cyanophenyl-sulfonyl chloride. Yield: 80% (LC).

LC-MS 480 (M+1)$^+$, 478 (M−1)$^−$

Example 7

N-{3-[2-(4-Aminoiminomethylphenyl)ethoxy]phenyl}-4-fluorobenzene-sulfonamide×HCl Prepared according to the procedure described in Example 4(v) above, using 4-fluorobenzenesulfonyl chloride instead of 2-cyanophenylsulfonyl chloride. Yield: 83% (LC).

LC-MS 414 (M+1)$^+$, 412 (M−1)$^−$

Example 8

N-{3-[2-(4-Aminoiminomethylphenyl)ethoxy]phenyl}-2,5-dimethylbenzene-sulfonamide×HCl Prepared according to the procedure described in Example 4(v) above, using 2,5-dimethylbenzenesulfonyl chloride instead of 2-cyanophenylsulfonyl chloride. Yield: 88% (LC).

LC-MS 424 (M+1)$^+$, 422 (M−1)$^−$

Example 9

N-{3-[2-(4-Aminoiminomethylphenyl)ethoxy]phenyl}-5-chlorothiophene-2-sulfonamide×HCl Prepared according to the procedure described in Example 4(v) above, using 5-chlorothiophene-2-sulfonyl chloride instead of 2-cyanophenylsulfonyl chloride. Yield: 67% (LC).

LC-MS 436 (M+1)$^+$, 434 (M−1)$^−$

Example 10

N-{3-[2-(4-Aminoiminomethylphenyl)ethoxy]phenyl}-1-methylimidazole-4-sulfonamide×HCl Prepared according to the procedure described in Example 4(v) above, using 1-methylimidazole-4-sulfonyl chloride instead of 2-cyanophenylsulfonyl chloride. Yield: 44% (LC).

LC-MS 400 (M+1)$^+$

Example 11

N-{3-[2-(4-Aminoiminomethylphenyl)ethoxy]phenyl}-3,5-dimethyl-isoxazole-4-sulfonamide×HCl Prepared according to the procedure described in Example 4(v) above, using 3,5-dimethylisoxazole-4- sulfonyl chloride instead of 2-cyanophenylsulfonyl chloride. Yield: 69% (LC).

LC-MS 415 (M+1)+, 413 (M−1)−

Example 12

N-{3-[2-(4-Aminoiminomethylphenyl)ethoxy] phenyl}benzlsulfonamide×HCl

Prepared according to the procedure described in Example 4(v) above, using benzylsulfonyl chloride instead of 2-cyanophenylsulfonyl chloride. Yield: 71% (LC).

LC-MS 410 (M+1)+, 408 (M−1)−

Example 13

N-{3-[2-(4-Aminoiminomethylphenyl)ethoxy] phenyl}-2,5-dichlorothiophene-3-sulfonamide×HCl Prepared according to the procedure described in Example 4(v) above, using 2,5-chlorothiophene-3-sulfonyl chloride instead of 2-cyanophenylsulfonyl chloride. Yield: 56% (LC).

LC-MS 471 (M+1)+

Example 14

N-{3-[2-(4-Aminoiminomethylphenyl)ethoxy]-5-methylphenyl}-2-chlorobenzenesulfonamide×HOAc The title compound was obtained as a side product from Example 22(iv) below. Yield: 0.014 g (13%).

LC-MS 444 (M+1)+

$^1$H NMR (500 MHz; CD$_3$OD): δ8.03 (dd, 1H), 7.75 (d, 2H), 7.50–7.55 (several peaks, 4H), 7.39 (m, 1H), 6.52 (t, 1H), 6.49 (t, 1H), 6.38 (t, 1H), 4.13 (t, 2H), 3.13 (t, 2H), 2.55 (t, 2H), 2.18 (s, 3H), 1.93 (s, 3H)

Example 15

N-{3,-[2-(4-Aminoiminomethylphenyl)ethoxy]-2-methylphenyl}-benzenesulfonamide×CF$_3$COOH (i) 3-t-Butoxycarbonylamino-2-methylphenol 3-Amino-2-methylphenol (2.0 g; 16 mmol) and di-t-butylcarbonate were dissolved in THF (20 mL) and refluxed overnight. Evaporation of the solvent followed by flash chromatography (SiO$_2$; EtOAc 5–30% in isohexane) afforded 2.48 g (69%) of the sub-title compound.

$^1$H NMR (300 MHz; CDCl$_3$): δ7.35 (d, 1H), 7.02 (t, 1H), 6.52 (d, 1H), 6.25 (s, 1H), 4.86 (s, 1H), 2.13 (s, 3H), 1.52 (s, 9H)

(ii) t-Butoxycarbonylamino-3-[2-(4-cyanophenyl) ethoxy]-2-methylbenzene

Triphenylphosphine (1.31 g, 13.5 mmol) and diethylazodicarboxylate (1.7 mL) were dissolved in THF (20 mL) under nitrogen. After 15 minutes 3-t-butoxycarbonylamino-2-methylphenol (2.48 g; 11.1 mmol; from step (i) above) dissolved in THF (20 mL) and 2-(4-cyanophenyl)ethanol (1.9 g, 13 mmol) were added. After 5 days at room temperature water was added and the stirring continued for 30 minutes. The mixture was extracted with EtOAc. The organic phase was washed with water and brine, dried (MgSO$_4$) and the solvent removed in vacuo. Purification by flash chromatography afforded 2.98 g (77%) of the sub-title compound.

$^1$H NMR (300 MHz; CDCl$_3$): δ7.4–7.8 (m, 5H), 7.10 (m, 1H), 6.63 (dd, 1H), 6.24 (s, 1H), 4.18 (t, 2H), 3.16 (t, 2H), 2.02 (s, 3H), 1.51 (s, 9H)

(iii) Amino-3-[2-(4-cyanophenyl)ethoxy]-2-methylbenzene t-Butoxycarbonylamino-3-[2-(4cyanophenyl)ethoxy]-2-methylbenzene (2.69 g, 7.64 mmol; from step (ii) above) were dissolved in EtOAc, pre-saturated with HCl(g), (150 mL) under nitrogen and stirred at room temperature overnight. After evaporation of the solvent the residue was partitioned between 10% aqueous HCl and EtOAc. The aqueous phase was washed with EtOAc, basified with NaOH (2M, aq.) and extracted with EtOAc. The combined organic phases were washed with brine, dried (MgSO$_4$) and the solvent evaporated to afford 0.42 g (19%) of the sub-title compound.

$^1$H NMR (300 MHz; CDCl$_3$): δ7.59 (d, 2H), 7.40 (d, 2H), 6.94 (t, 1H), 6.31 (dd, 2H), 3.61 (s, 2H), 4.12 (t, 2H), 3.15 (t, 2H), 1.96 (s, 3H)

(iv) N-{3-[2-(4-Cyanophenyl)ethoxy]-2-methylphenyl}benzene-sulfonamide

Benzenesulfonyl chloride (0.24 mL; 1.9 mmol) was added to a stirred solution of amino-3-[2-(4-cyanophenyl)ethoxy]-2-methylbenzene (0.42 g; 1.7 mmol; from step (iii) above) in dry pyridine (20 mL) under nitrogen. The reaction was left overnight at room temperature. After evaporation of the solvent the residue was partitioned between 10% aqueous HCl and EtOAc. The organic layer was washed with brine, dried (MgSO$_4$) and the solvent removed in vacuo. Purification by flash chromatography afforded 0.47 g (72%) of the sub-title compound.

$^1$H NMR (300 MHz; DMSO-d$_6$): δ7.4–7.8 (m, 10H), 7.00 (t, 1H), 6.80 (d, 1H), 6.50 (d, 1H), 4.16 (t, 2H), 3.10 (t, 2H), 1.72 (s, 3H)

(v) N-{3-[2-(4-Aminoiminomethylphenyl)-ethoxy]-2-methyl-phenyl}-benzenesulfonamide×CF$_3$COOH N-{3-[2-(4-Cyanophenyl)ethoxy]-2-methylphenyl}benzenesulfonamide (0.47 g; 1.2 mmol; from step (iv) above) was added to a saturated solution of HCl(g) in EtOH (150 mL) and the solution was stirred for 2 days. The solvent was removed by rotary evaporation and the residue treated with EtOH, pre-saturated with NH$_3$(g), for 3 days. After removal of the solvent, the crude product was purified by preparative HPLC (5–95% MeOH:0.1% trifluoroacetic acid). Recrystallization from isopropanol afforded 0.056 g (9%) of the title compound.

LC-MS 410 (M+1)+

$^1$H NMR (300 MHz; DMSO-d$_6$): δ9.55 (bs, 1H), 9.25 (bs, 2H), 9.0 (bs, 2H), 7.75 (d, 2H), 7.50–7.70 (several peaks, 7H), 6.99 (t, 1H), 6.80 (dd, 1H), 6.45 (dd, 1H), 4.09 (t, 2H), 3.15 (t, 2H), 1.82 (s, 3H)

Analysis calculated for C$_{24}$H$_{24}$F$_3$N$_3$O$_5$S: C, 55.06%; H, 4.62%; N, 8.03%; S, 6.12. Found: C, 54.83; H, 4.64%; N, 7.97%; S, 6.12%

Example 16

N-{5-[2-(4-Aminoiminomethylphenyl)ethoxy]-2-methylphenyl}benzene-sulfonamide×HCl (i) [2-(4-Cyanophenyl)ethoxy]-4-methyl-3-nitrobenzene 4-Methyl-3-nitrophenol (0.765 g; 5.0 mmol), 2-(4-cyanophenyl)ethanol (0.735 g; 5.0 mmol) and diethylazodicarboxylate (0.87 g; 5.0 mmol) were dissolved in THF (20 mL). Triphenylphosphine (1.31 g; 5.0 mmol), dissolved in THF (5 mL), was added and the solution stirred overnight. Evaporation in vacuo and the addition of diethyl ether afforded a yellow solid that was recrystallized from water-:acetone (9:1), affording the sub-title compound as yellowish crystals. Yield: 1.04 g (74%).

$^1$H NMR (400 MHz; CDCl$_3$): δ7.63 (d, 2H), 7.50 (d, 1H), 7.42 (d, 2H), 7.23 (d, 1H), 7.04 (dd, 1H), 4.14 (t, 2H), 3.09 (t, 2H), 2.53 (s, 3H)

(ii) Amino-5-[2-(4-cyanophenyl)ethoxy]-2-methylbenzene

Sodium borohydride (0.127 g; 3.35 mmol) was added in portions to a cold suspension (ice:water temperature) of [2-(4-cyanophenyl)ethoxy]-4-methyl-3-nitrobenzene (0.19 g; 0.67 mmol; from step (i) above) and aqueous copper sulfate (1.34 mL; 1M; 1.34 mmol) in EtOH (5 mL) over five minutes. The temperature was allowed to rise to ambient and the stirring continued for 30 minutes. Addition of EtOAc (50 mL) and filtration through Celite afforded a clear solution that was washed with water, dried (K$_3$CO$_3$) and concentrated in vacuo. Flash chromatography (SiO$_2$; toluene:EtOAc (10:1)) afforded 0.044 g (26%) of the sub-title compound as a white solid.

$^1$H NMR (400 MHz; CDCl$_3$): δ7.61 (d, 2H), 7.40 (d, 2H), 6.95 (d, 1H), 6.25–6.30 (m, 2H), 4.16 (t, 2H), 3.60 (bs, 2H), 3.13 (t, 2H), 2.12 (s, 3H)

(iii) N-{5-[2-(4-Cyanophenyl)ethoxy]-2-methylphenyl}benzenesulfonamide

Benzenesulfonyl chloride (22 μL; 0.17 mmol) was added to a cold solution (ice :water temperature) of amino-5-[2-(4-cyanophenyl)ethoxy]-2-methyl-benzene (0.041 g; 0.16 mmol; from step (ii) above) in pyridine (4 mL) The reaction flask was left overnight in a refrigerator. NaHCO$_3$/aq (sat.) was added and the solution extracted twice with EtOAc. The combined organic phases were washed with water, HCl/aq (2M) and water. Drying (MgSO$_4$) and evaporation of the solvent in vacuo afforded 0.062 g (100%) of the sub-title compound.

$^1$H NMR (500 MHz; CDCl$_3$): δ7.78 (d, 2H), 7.66 (d, 2H), 7.59 (t, 1H), 7.43–7.50 (m, 4H), 7.02 (d, 1H), 6.99 (d, 1H), 6.65 (dd, 1H), 6.51 (bs, 1H), 4.18 (t, 2H), 3.17 (t, 2H), 1.91 (s, 3H)

(iv) N-{5-[2-(4-Ethoxyiminomethylphenyl)ethoxy]-2-methylphenyl}-benzenesulfonamide×HCl To a cooled (ice:water temperature) saturated solution of HCl(g) in EtOH (5 mL) was added N-{5-[2-(4-cyanophenyl)ethoxy]-2-methyl-phenyl}benzene-sulfonamide (0.062 g; 0.16 mmol; from step (iii) above). After 30 minutes the temperature was allowed to rise to ambient and the stirring was continued for 20 hours. Evaporation of the solvent afforded the sub-title compound in a quantitative yield. To remove traces of HCl, EtOH was added and evaporated.

LC-MS 439 (M+1)$^+$ (v) N-{5-[2-(4-Aminoiminomethylphenyl)ethoxy]-2-methylphenyl}-benzenesulfonamide×HCl N-{5-[2-(4-Ethoxyiminomethylphenyl)ethoxy]-2-methylphenyl}benzene-sulfonamide×HCl (0.076 g; 0.16 mmol; from step (iv) above) was dissolved in MeOH, pre-saturated with NH$_3$(g), and stirred at room temperature for 20 hours. After evaporation of the solvent in vacuo the residue was redissolved in EtOH and the solvent evaporated to remove HCl(g). Trituration of the residue with methylene chloride afforded 0.045 g (62%) of the title compound.

LC-MS 410 (M+1)$^+$ $^1$H NMR (400 MHz; CD$_3$OD): δ7.75 (d, 2H), 7.65 (d, 2H), 7.50–7.60 (m, 3H), 7.45 (t, 2H), 6.95 (d, 1H), 6.60–6.70 (m, 2H), 4.09 (t, 2H), 3.13 (t, 2H), 1.85 (s, 3H)

Example 17

N-{3-[2-(4-Aminoiminomethylphenyl)ethoxy]-5-methylphenyl}benzene-sulfonamide×HCl (i) t-Butyloxycarbonylamino-3-hydroxy-5-methylbenzene The sub-title compound was prepared according to the method described in Example 1(i) above from amino-3-hydroxy-5-methylbenzene (8.0 g; 65 mmol). Yield: 13.2 g (91%).

$^1$H NMR (400 MHz; CDCl$_3$): δ6.83 (bs, 1H), 6.62 (s, 1H), 6.54 (bs, 1H), 6.39 (bs, 1H), 6.37 (s, 1H), 2.22 (s, 3H) 1.50 (s, 9H)

(ii) t-Butyloxycarbonylamino-3-[2-(4-cyanophenyl)ethoxy]-5-methylbenzene

The sub-title compound was prepared according to the method described in Example (ii) above from t-butyloxycarbonylamino-3-hydroxy-5-methyl-benzene (5.9 g; 26.4 mmol; from step (i) above). Yield: 6.21 g (67%).

$^1$H NMR (400 MHz; CDCl$_3$): δ7.58 (d, 2H), 7.38 (d, 2H), 6.93 (t, 1H), 6.63 (t, 1H), 6.44 (bs, 1H), 6.37 (t, 1H), 4.16 (t, 2H), 3.11 (t, 2H), 2.25 (s, 3H), 1.50 (s, 9H)

$^{13}$C NMR (100 MHz; CDCl$_3$): δ159.2, 152.6, 144.3, 140.0, 139.4, 132.2, 129.8, 119.0, 111.8, 110.4, 110.3, 101.9, 80.5, 67.6, 35.9, 28.4, 21.6

(iii) Amino-3-[2-(4-cyanophenyl)ethoxy]-5-methylbenzene t-Butyloxycarbonylamino-3-[2-(4-cyanophenyl)ethoxy]-5-methylbenzene (1.55 g; 4.4 mmol; from step (ii) above) was stirred in a mixture of trifluoroacetic acid (10 mL) and methylene chloride (10 mL) for 3 hours. The solvent was removed in vacuo. The residue was dissolved in EtOAc (50 mL), washed with Na$_2$CO$_3$/aq (sat.) and water, dried (Na$_2$CO$_3$) and the solvent was removed to afford a yellow oil, which crystallized upon standing. Yield: 1.19 g (100%).

$^1$H NMR (500 MHz; CDCl$_3$): δ7.60 (d, 2H), 7.38 (d, 2H), 6.10–6.15 (m, 2H), 6.03 (t, 1H), 4.14 (t, 2H), 3.12 (t, 2H), 2.20 (s, 3H)

(iv) N-{3-[2-(4-Cyanophenyl)ethoxy]-5-methylphenyl}benzenesulfonamide

To a cold solution (ice:water temperature) of amino-[3-2-(4-cyanophenyl)ethoxy]-5-methylbenzene (0.13 g; 0.50 mmol; from step (iii) above) in pyridine (5 mL) was added benzenesulfonyl chloride (71 μL; 0.55 mmol). After 2 hours stirring, NaHCO$_3$/aq (sat.) was added, and the solution extracted with EtOAc. The combined organic phases were dried (MgSO$_4$) and the solvent removed in vacuo. The residue was purified by flash chromatography (SiO$_2$; EtOAc:heptane (1:1)) to give 0.19 g (97%) of the sub-title compound.

$^1$H NMR (500 MHz; CDCl$_3$): δ7.82 (d, 2H), 7.62 (d, 2H), 7.58 (t, 1H), 7.47 (t, 2H), 7.39 (d, 2H), 6.88 (bs, 1H), 6.56 (t, 1H), 6.40–6.45 (m, 2H), 4.15 (t, 2H), 3.14 (t, 2H), 2.22 (s, 3H)

(v) N-{3-[2-(4-Ethoxyiminomethylphenyl)ethoxy]-5-methylphenyl}-benzenesulfonamide×HCl N-{3-[2-(4-Cyanophenyl)ethoxy]-5-methylphenyl}benzenesulfonamide (0.19 g; 0.50 mmol; from step (iv) above) was added to a cooled (ice:water temperature) saturated solution of HCl(g) in EtOH (5 mL). After 30 minutes the temperature was allowed to rise to ambient temperature and the stirring was continued for 24 hours. Evaporation of the solvent afforded the sub-title compound in a quantitative yield.

$^1$H NMR (500 MHz; CDCl$_3$): δ12.3 (bs, 1H), 11.7 (bs, 1H), 8.27 (d, 2H), 8.02 (bs, 1H), 7.90 (d, 2H), 7.35–7.50 (several peaks, 5H), 6.63 (t, 1H), 6.57 (t, 1H), 6.41 (t, 1H), 4.95 (q, 2H), 4.08 (t, 2H), 3.12 (t, 2H), 2.20 (s, 3H) 1.62 (t, 3H)

(vi) N-{3-[2-(4-Aminoiminomethylphenyl)ethoxy]-5-methylphenyl}-benzenesulfonamide×HCl N-{3-[2-(4-Ethoxyiminomethylphenyl)ethoxy]-5-methylphenyl}benzene-sulfonamide×HCl (0.22 g; 0.50 mmol; from step (v) above) was dissolved in MeOH, saturated with NH$_3$(g), and stirred at room temperature for 24 hours. After evaporation of the solvent in vacuo the residue was redissolved in MeOH (5 mL) and the solution acidified to pH 1 with EtOH, saturated with HCl(g). The solvent was evaporated and the residue dissolved in MeOH (5 mL). Upon addition of dry Et$_2$O, white crystals precipitated, which were filtered off, affording 0.145 g (65%) of the title compound.

LC-MS 410 (M+1)$^+$ $^1$NMR (500 MHz; CD$_3$OD): δ9.25 (bs, 2H), 8.75 (bs, 2H), 7.77–7.82 (m, 4H), 7.55–7.61 (m, 3H), 7.48–7.53 (m, 2H), 6.57 (t, 1H), 6.45–6.50 (m, 2H), 4.18 (t, 2H), 4.15 (t, 2H), 2.20 (s, 3H)

Example 18

N-{3-[2-(4-Aminoiminomethylphenyl)ethylthio]phenyl}benzenesulfonamide×HCl (i) 4-Toluenesulfonic acid-2-(4-cyanophenyl)ethyl ester 2-(4-Cyanophenyl)ethanol (1.46 g; 9.9 mmol) and 4-toluenesulfonyl chloride (1.9 g; 10 mmol) were stirred in pyridine (20 mL) at 5° C. for 3 hours. Work-up was performed by removing the solvent, addition of 2M aqueous HCl and extraction with EtOAc. The organic phase was washed with aqueous citric acid, then passed through a short plug of silica gel with Et$_2$O. Removal of the solvent in vacuo afforded a colourless oil, containing ca. 30% of unreacted 2-(4-cyanophenyl)ethanol according to $^1$H NMR. The oil was further subjected to the reaction conditions above for 2 hours. Work-up as above afforded 2.0 g (66%) of the sub-title compound as a yellow solid.

$^1$H NMR (300 MHz; CDCl$_3$): δ7.65 (d, 2H), 7.55 (d, 2H), 7.16 (d, 2H), 7.10 (d, 2H), 4.24 (t, 2H), 3.07 (t, 2H), 2.45 (s, 3H)

(ii) Amino-3-[2-(4- cyanophenyl)ethylthio]benzene

3-Aminothiophenol (0.87 g; 7.0 mmol), 4-toluenesulfonic acid-2-(4-cyano-phenyl) ethyl ester (2.0 g; 6.6 mmol; from step (i) above) and K$_2$CO$_3$ (1 g) were stirred in a mixture of EtOH (10 mL) and CH$_2$Cl$_2$ for 4 hours. Addition of ether, washing with brine and 2M aqueous NaOH, drying (MgSO$_4$), evaporation of the solvent and flash chromatography (SiO$_2$; Et$_2$O:hexane (1:1)) afforded 0.82 g (49%) of the sub-title compound.

$^1$H NMR (300 MHz; CDCl$_3$): δ7.60 (d, 2H), 7.30 (d, 2H), 7.08 (t, 1H), 6.75 (dd, 1H), 6.71 (t, 1H), 6.53 (dd, 1H), 3.7 (bs, 2H), 3.13 (t, 2H), 2.96 (t, 2H)

(iii) N-{3-[2-(4-Cyanophenyl)ethylthio]phenyl}benzenesulfonamide

Benzenesulfonyl chloride (0.62 g; 3.5 mmol) was added to a cold solution (ice:water temperature) of amino-3-[2-(4-cyanophenyl)ethylthio]benzene (0.80 g; 3.15 mmol; from step (ii) above) in a mixture of pyridine (1 mL) and CH$_2$Cl$_2$ (20 mL) over 10 minutes. After 3 hours stirring, 2M aqueous HCl was added and the solution extracted with CH$_2$Cl$_2$. The organic layer was dried (MgSO$_4$) and the solvent removed in vacuo. The residue was purified by flash chromatography (SiO$_2$; Et$_2$O:hexane (1:1)) to give 1.02 g (82%) of the sub-title compound.

LC-MS 395 (M+1)$^+$, 393 (M−1)$^-$ $^1$H NMR (300 MHz; CDCl$_3$): δ7.80 (d, 2H), 7.60 (d, 2H), 7.4–7.6 (m, 3H), 7.30 (s, 1H), 7.0–7.2 (m, 3H), 6.80 (m, 2H), 3.11 (t, 2H), 2.93 (t, 2H)

(iv) N-{3-[2-(4-Aminoiminomethylphenyl)ethylthio]phenyl}benzene-sulfonamide×HCl

Trimethyl aluminum (2.5 mL; 2M in toluene; 5.0 mmol) was added to a cold (ice:water temperature) saturated suspension of NH$_4$Cl (0.29 g; 5.4 mmol) in toluene. After 30 minutes stirring, N-{3-[2-(4-cyanophenyl)ethyl-thio]phenyl}benzenesulfonamide (1.0 g; 2.6 mmol; from step (iii) above), dissolved in toluene, was added and the mixture was refluxed for 12 hours. The reaction mixture was poured into silica gel (10 g) and CHCl$_3$ (30 mL). The solids were removed by filtration and washed with methanol. The combined liquid phases were concentrated in vacuo to give a solid residue. The material was purified twice by p reparative HPLC (MeOH:NH$_4$OAc (0.1M aq.)) to obtain the acetate, which was dissolved in MeOH, pre-saturated with HCl(g), three times, and evaporated to afford the title compound as a white solid. Yield: 0.63 g (54%).

mp 84–7° C.

LC-MS 412 (M+1)$^+$ $^1$H NMR (300 MHz; DMSO-d$_6$): δ10.45 (bs, 1H), 9.33 (bs, 2H), 9.10 (bs, 2H), 7.75 (m, 4H), 7.0–7.6 (m, 9H), 3.17 (t, 2H), 2.90 (t, 2H)

Example 19

N-(2-Chlorophenyl)sulfonyl-3-[2-(4-aminoiminomethylphenyl)ethoxy]-5-methylphenylaminoacetic acid, ethyl, ester×HOAc (i) 3-[2-(4-Cyanophenyl)ethoxy]-5-methylphenylaminoacetic acid, ethylester Ethyl bromoacetate (134 μL, 1.2 mmol) was added to a suspension of amino-3-[2-(4-cyanophenyl)ethoxy]-5-methylbenzene (0.252 g; 1.00 mmol; from Example 17(iii) above) and K$_2$CO$_3$ (0.165 g; 1.2 mmol) in DMF (10 mL), and the mixture was stirred for 20 hours. The solvent was removed in vacuo and the residue partitioned between water and EGO. After separation, the aqueous phase was extracted once with Et$_2$O. The combined ether phases were washed with water and brine, dried (MgSO$_4$) and the solvent was removed in vacuo. The residue was purified by flash chromatography (SiO$_2$; EtOAc:heptane (3:7)) to give 0.30 g (89%) of the sub-title compound, a colourless oil which crystallized upon standing.

$^1$H NMR (400 MHz; CDCl$_3$): δ7.60 (d, 2H), 7.40 (d, 2H), 6.15 (t, 1H), 6.08 (t, 1H), 5.97 (t, 1H), 4.25 (q, 2H), 4.16 (t, 2H), 3.95 (s, 2H), 3.14 (t, 2H), 2.23 (s, 3H), 1.30 (t, 3H)

(ii) N-(2-Chlorophenyl)sulfonyl-3-[2-(4-cyanophenyl)ethoxy]-5-methyl-phenylaminoacetic acid, ethyl ester 2-Chlorobenzenesulfonyl chloride (0.225 g; 1.06 mmol) was added to a cold solution (ice:water temperature) of 3-[2-(4-cyanophenyl)ethoxy]-5-methyl-phenylaminoacetic acid, ethyl ester (0.30 g; 0.88 mmol; from step (i) above) in pyridine (10 mL). After 2 hours stirring the temperature was allowed to rise to ambient. After 4 hours at this temperature more 2-chloro-benzenesulfonyl chloride (0.056 g; 0.26 mmol) was added and the mixture was left overnight. The mixture was then poured into aqueous saturated NaHCO$_3$ and extracted twice with Et$_2$O. The combined ether phases where washed with HCl/aq (2M), H$_2$O and brine, dried (MgSO$_4$) and the solvent removed in vacuo. The residue was purified by flash chromatography (SiO$_2$; EtOAc:heptane (1:3)) to give 0.28 g (62%) of the sub-title compound.

$^1$H NMR (500 MHz; CDCl$_3$): δ7.90 (dd, 1H), 7.61 (d, 2H), 7.53 (dd, 1H), 7.45 (m, 1H), 7.39 (dd, 2H), 7.25 (m, 1H), 6.73 (t, 1H), 6.62 (t, 1H), 6.58 (t, 1H), 4.62 (s, 2H), 4.19 (q, 2H), 4.08 (t, 2H), 3.08 (t, 2H), 2.19 (s, 3H) 1.27 (t, 3H)

(iii) N-(2-Chlorophenyl)sulfonyl-3-[2-(4-ethoxyiminomethylphenyl)-ethoxy]-5-methylphenylaminoacetic acid, ethyl ester×HCl N-(2-Chlorophenyl)sulfonyl-3-[2-(4-cyanophenyl) ethoxy]-5-methylphenyl-aminoacetic acid, ethyl ester (0.27 g; 0.53 mmol; from step (ii) above) was added to a saturated solution of HCl(g) in EtOH (100 mL) and the solution was stirred for 20 hours. Evaporation of the solvent afforded the sub-title compound in a quantitative yield.

LC-MS 559 (M+1)$^+$ (iv) N-(2-Chlorophenyl)sulfonyl-3-[2-(4-aminoiminomethylphenyl)ethoxy]-5-methylphenylaminoacetic acid, ethyl ester×HOAc N-(2-Chlorophenyl)sulfonyl-3-[2-(4-ethoxyiminomethylphenyl)ethoxy]-5-methylphenylaminoacetic acid, ethyl ester×HCl (0.32 g; 0.53 mmol; from step (iii) above) was dissolved in MeOH (pre-saturated with NH$_3$(g)), and stirred at room temperature for 2 days. After evaporation of the solvent in vacuo, the residue was redissolved in EtOH and the solution acidified to pH 1 with EtOH (saturated with HCl(g)). The solvent was evaporated and the residue purified by preparative HPLC (30–60% CH$_3$CN:0.1M NH$_4$OAc) to afford 0.038 g (12%) of the title compound.

LC-MS 530 (M+1)$^+$ $^1$H NMR (400 MHz; CD$_3$OD): δ7.83 (dd, 1H), 7.75 (d, 2H), 7.50–7.63 (several peaks, 4H), 7.36 (m, 1H), 6.71 (t, 1H), 6.60 (m, 2H), 4.62 (s, 2H), 4.17 (q, 2H), 4.12 (t, 2H), 3.12 (t, 2H), 2.16 (s, 3H), 1.90 (s, 3H), 1.22 (t, 3H)

Example 20

N-(2-Chlorophenyl)sulfonyl-3-[2-(4-aminoiminomethylphenyl)ethoxy]-5-methylphenylaminoacetamide×HOAc The title compound was obtained as a side product in Example 19 above. Yield: 0.036 g (12%).

LC-MS 501 (M+1)$^+$ $^1$H NMR (400 MHz; CD$_3$OD): δ7.83 (dd, 1H), 7.75 (d, 2H), 7.50–7.63 (several peaks, 4H), 7.34 (m, 1H), 6.72 (t, 1H), 6.60 (m, 2H), 4.53 (s, 2H), 4.15 (t, 2H), 3.12 (t, 2H), 2.16 (s, 3H), 1.90 (s, 3H)

Example 21

N-(2-Chlorophenyl)sulfonyl-3-[2-(4-aminoiminomethylphenyl)ethoxy]-5-methylphenylaminoacetic acid×HOAc N-(2-Chlorophenyl)sulfonyl-3-[2-(4-aminoiminomethylphenyl)ethoxy]-5-methylphenylaminoacetic acid, ethyl ester×HOAc (0.030 g; 0.050 mmol; from Example 19 above) was stirred in a mixture of THF (3 mL) and 2M LiOH/aq (3 mL) for 4 hours. THF was removed in vacuo and the resultant suspension was acidified to pH 3 by the addition of HCl/aq (2M). CH$_3$CN was added to dissolve the solid phase. Purification by preparative HPLC (30% CH$_3$CN:0.1M NH$_4$OAc) afforded 0.011 g (46%) of the title compound.

LC-MS 502 (M+1)$^+$, 500 (M−1)$^−$ $^1$H NMR (500 MHz; CD$_3$OD): δ7.86 (dd, 1H), 7.75 (d, 2H), 7.58 (d, 1H), 7.52 (m, 3H), 7.34 (dt, 1H), 6.78 (t, 1H), 6.58 (t, 1H), 6.53 (t, 1H), 4.40 (s, 2H), 4.18 (t, 2H), 3.12 (t, 2H), 2.12 (s, 3H), 1.98 (s, 3H)

Example 22

N-(2-Chlorophenyl)sulfonyl-2-{3-[2-(4-aminoiminomethylphenyl)ethoxy]-5-methylphenylamino}propanoic acid, ethyl ester× HOAc (i) 2-{3-[2-(4-Cyanophenyl)ethoxy]-5-methylphenylamino}propanoic acid, ethyl ester Amino-3-[2-(4-cyanophenyl)ethoxy]-5-methylbenzene (0.252 g; 1.00 mmol; from Example 17(iii) above), ethyl acrylate (130 μL; 1.2 mmol) and acetic acid (9 μL; 0.15 mmol) were refluxed together for 8 hours. After evaporation in vacuo, the resultant black oil was purified by flash chromatography (SiO$_2$; EtOAc:heptane (3:7)) to give 0.102 g (29%) of the sub-title compound.

$^1$H NMR (500 MHz; CDCl$_3$): δ7.62 (d, 2H), 7.41 (d, 2H), 6.13 (t, 1H), 6.10 (t, 1H), 5.99 (t, 1H), 4.15–4.20 (several peaks, 4H), 3.43 (t, 2H), 3.14 (t, 2H), 2.61 (t, 2H), 2.23 (s, 3H), 1.30 (t, 3H)

(ii) N-(2-Chlorophenyl)sulfonyl-2-{3-[2-(4-cyanophenyl)ethoxy]-5-methylphenylamino}propanoic acid, ethyl ester The sub-title compound was prepared according to the method described in Example 19(ii) above from 2-{3-[2-(4-cyanophenyl)ethoxy]-5-methylphenyl-amino}propanoic acid, ethyl ester (0.100 g; 0.28 mmol; from step (i) above) to afford 0.120 g (81%) of a yellowish oil.

$^1$H NMR (500 MHz; CDCl$_3$): δ7.85 (dd, 1H), 7.61 (d, 2H), 7.40–7.55 (several peaks, 2H), 7.38 (d, 2H), 7.25 (m, 1H), 6.67–6.70 (m, 3H), 4.07–4.15 (several peaks, 6H), 3.10 (t, 2H), 2.58 (t, 2H), 2.20 (s, 3H), 1.22 (t, 3H)

(iii) N-(2-Chlorophenyl)sulfonyl-2-{3-[2-(4-ethoxyiminomethylphenyl)-ethoxy]-5-methylphenylamino}propanoic acid, ethyl ester× HCl The sub-title compound was prepared according to the method described in Example 19(iii) above from N-(2- chlorophenyl)sulfonyl-2-{3-[2-(4-cyano-phenyl)ethoxy]-5-methylphenylamino}propanoic acid, ethyl ester (0.12 g;, 0.22 mmol; from step (ii) above) to afford 0.13 g (100%) as an oil.

LC-MS 572 (M+1)⁺

(iv) N-(2-Chlorophenyl)sulfonyl-2-{3-[2-(4-aminoiminomethylphenyl)-ethoxy]-5-methylphenylamino}-propanoic acid, ethyl ester× HOAc The title compound was prepared according to the method described in Example 19(iv) above from N-(2-chlorophenyl)sulfonyl-2-{3-[2-(4-ethoxy-iminomethylphenyl)ethoxy]-5-methylphenylamino}propanoic acid, ethyl ester×HCl (0.13 g; 0.22 mmol; from step (iii) above). Yield: 0.009 g (7%).

LC-MS 543 (M+1)⁻

¹H NMR (400 MHz; CD₃OD): δ7.70–7.80 (several peaks, 3H), 7.50–7.62 (several peaks, 4H), 7.35 (m, 1H), 6.62 (t, 1H), 6.55–6.60 (m, 2H), 4.10–4.17 (several peaks, 4H), 4.03 (q, 2H), 3.13 (t, 2H), 2.50 (t, 2H), 2.18 (s, 3H), 1.90 (s, 3H), 1.19 (t, 3H)

Example 23

N-(2-Chlorophenyl)sulfonyl-2-{3-[2-(4-aminoiminomethylphenyl)ethoxy]-5-methylphenylamino}propanamide×HOAc The title compound was obtained as a side product in Example 22 above.

Yield: 0.0065 g (5%).

LC-MS 514 (M+1)⁺

¹H NMR (400 MHz; CD₃OD): δ7.70–7.80 (several peaks, 3H), 7.50–7.65 (several peaks, 4H), 7.35 (m, 1H), 6.62 (t, 1H), 6.59 (t, 1H), 6.55 (t, 1H), 4.10–4.17 (several peaks, 4H), 3.13 (t, 2H), 2.45 (t, 2H), 2.2 (bs, 2H), 2.18 (s, 3H), 1.92 (s, 3H)

Example 24

N-(2-Chlorophenyl)sulfonyl-2-{3-[2-(4-aminoiminomethylphenyl)ethoxy]-5-methylphenylamino}propanoic acid×HOAc The title compound was prepared according to the method described in Example 21 above from N-(2-chlorophenyl)sulfonyl-2-{3-[2-(4-aminoimino-methylphenyl)ethoxy]-5-methylphenylamino}propanoic acid, methyl ester×HOAc (0.015 g; 0.025 mmol; from Example 25 below) to afford 0.007 g (48%) of a white solid.

LC-MS 516 (M+1)⁺

¹H NMR (500 MHz; CD₃OD): δ7.85 (d, 1H), 7.77 (d, 2H), 7.55–7.62 (several peaks, 4H), 7.35 (m, 1H), 6.65 (t, 1H), 6.60 (t, 1H), 6.53 (t, 1H), 4.19 (t, 2H), 4.02 (t, 2H), 3.16 (t, 2H), 2.38 (t, 2H), 2.22 (s, 3H), 1.97 (s, 3H)

Example 25

N-(2-Chlorophenyl)sulfonyl-2-{3-[2-(4-aminoiminomethylphenyl)-ethoxy]-5-methylphenylamino}propanoic acid, methyl ester× HOAc The title compound was obtained as a side product in Example 22(iv) above.

E Yield: 0.024 g (19%)

LC-MS 530 (M+1)⁺

¹H NMR (500 MHz; CD₃OD): δ7.75–85 (several peaks, 3H), 7.50–7.65 (several peaks, 4H), 7.37 (m, 1H), 6.69 (t, 1H), 6.56–6.60 (m, 2H), 4.12–4.20 (several peaks, 4H), 3.60 (s, 3H), 3.15 (t, 2H), 2.55 (t, 2H), 2.22 (s, 3H), 1.93 (s, 3H)

Example 26

N-(2-Chlorophenyl)sulfonyl-3-{3-[2-(4-aminoiminomethylphenyl)ethoxy]-5-methylphenylamino}butanoic acid, ethyl ester× HOAc

(i) 3-[2-(4-Cyanophenyl)ethoxy]-5-methylphenyl-2-chlorobenzenesulfonamide

2-Chlorophenylsulfonyl chloride (0.152 g; 0.72 mmol) was added to a cooled solution (ice:water temperature) of amino-3-[2-(4-cyanophenyl)ethoxy]-5-methylbenzene (0.16 g; 0.60 mmol; from Example 17(iii) above) in pyridine (5 mL), and the resultant orange solution was stirred for 4 hours. Addition of H₂O (30 mL), extraction with EtOAc, drying (MgSO₄), evaporation of the solvent, and purification by flash chromatography (SiO₂; 25–33% EtOAc:hexane) yielded 0.20 g (78%) of the sub-title compound.

²H NMR (500 MHz; CDCl₃): δ8.03 (d, 1H), 7.61 (d, 2H), 7.45–7.53 (m, 2H), 7.32–7.40 (m, 3H), 7.00 (s, 1H), 6.56 (t, 1H), 6.47 (t, 1H), 6.41 (t, 1H), 4.10 (t, 2H), 3.08 (t, 2H), 2.19 (s, 3H)

(ii) N-(2-Chlorophenyl)sulfonyl-3-{3-[2-(4-cyanophenyl)ethoxy]-5-methyl-phenylamino}butanoic acid, ethyl ester Ethyl 3-bromobutanoate (87 μL; 0.60 mmol) was added to a suspension of 3-[2-(4-cyanophenyl)ethoxy]-5-methylphenyl-2-chlorobenzenesulfonamide (0.171 g; 0.40 mmol; from step (i) above) and K₂CO₃ (0.166 g; 1.2 mmol) in DMF (10 mL). The mixture was stirred overnight, then poured into water, extracted with Et₂O, dried (MgSO₄), and the solvent was removed in vacuo. The residue was purified by flash chromatography (SiO₂; EtOAc:hexane (3:7)) to give 0.195 g (90%) of the sub-title compound as a colourless oil.

¹H NMR (400 MHz; CDCl₃): δ7.85 (dd, 1H), 7.61 (d, 2H), 7.40–7.52 (several peaks, 2H), 7.38 (d, 2H), 7.25 (m, 1H), 6.67–6.70 (m, 3H), 4.07–4.15 (several peaks, 4H), 3.85 (t, 2H), 3.10 (t, 2H), 2.40 (t, 2H), 2.20 (s, 3H), 1.80 (m, 2H), 1.22 (t, 3H)

(iii) N-(2-Chlorophenyl)sulfonyl-3-{3-[2-(4-ethoxyiminomethylphenyl)-ethoxy]-5-methylphenylamino}butanoic acid, ethyl ester×HCl The sub-title compound was prepared according to the method described in Example 19(iii) above from N-(2-chlorophenyl)sulfonyl-3-{3-[2-(4-cyano-phenyl)ethoxy]-5-methylphenylamino}butanoic acid, ethyl ester (0.195 g; 0.36 mmol; from step (ii) above) to afford 0.22 g (100%) of a white foam.

¹H NMR (500 MHz; CDCl₃): δ12.5 (bs, 1H), 11.8 (bs, 1H), 8.35 (d, 2H), 7.82 (dd, 1H), 7.40–7.50 (several peaks, 4H), 7.23 (m, 1H), 6.58 (t, 1H), 6.55 (t, 1H), 6.50 (t, 1H), 4.95 (q, 2H), 4.02–4.10 (several peaks, 4H), 3.87 t, 2H), 3.10 (t, 2H), 2.40 (t, 2H), 2.20 (s, 3H), 1.80 (m, 2H), 1.60 (t, 3H), 1.22 (t, 3H)

(iv) N-(2-Chlorophenyl)sulfonyl-3-{3-[2-(4-aminoiminomethylphenyl)-ethoxy]-5-methylphenylamino}butanoic acid, ethyl ester× HOAc The title compound was prepared according to the method described in Example 19(iv) above from N-(2-chlorophenyl)

sulfonyl-3-{3-[2-(4-ethoxy-iminomethylphenyl)ethoxy]-5-methylphenylamino}butanoic acid, ethyl ester×HCl (0.22 g; 0.36 mmol; from step (iii) above). Yield: 0.063 g (28%).

LC-MS 557 (M+1)$^+$ $^1$H NMR (400 MHz; CD$_3$OD): δ7.78 (dd, 1s), 7.76 (d, 2H), 7.50–7.60 (several peaks, 4H), 7.33 (m, 1H), 6.63 (t, 1H), 6.58 (t, 1H), 6.56 (t, 1H), 4.15 (t, 2H), 4.07 (q, 2H), 3.87 (t, 2H), 3.13 (t, 2H), 2.41 (t, 2H), 2.18 (s, 3H), 1.90 (s, 3H), 1.74 (m, 2H), 1.21 (t, 3H)

Example 27

N-(2-Chlorophenyl)sulfonyl-3-{3-[2-(4aminoiminomethylphenyl)ethoxy]-5-methylphenylamino}butanamide×HOAc NH$_3$(g) was fed into cold MeOH (CO$_2$(S):acetone temperature) until a ca. 1:1 solution was obtained. The solution was placed in an autoclave with N-(2-chlorophenyl) sulfonyl-3-{3-[2-(4-aminoiminomethylphenyl)ethoxy]-5-methylphenylamino}butanoic acid, ethyl ester×HOAc (0.027 g; 0.044 mmol) and NaCN (0.001 g). The closed system was heated to 50° C. for 4 days. After cooling, the solvent was removed in vacuo and the residue purified by preparative HPLC (30% CH$_3$CN:0.1M NH$_4$OAc) to afford 0.021 g (81%) of the title compound.

LC-MS 529 (M+1)$^+$ $^1$H NMR (400 MHz; CD$_3$OD): δ7.70–80 (several peaks, 3H), 7.50–7.60 (several peaks, 4H), 7.33 (m, 1H), 6.62 (t, 1H), 6.59 (t, 1H), 6.55 (t, 1H), 4.12 (t, 2H), 3.85 (t, 2H), 3.12 (t, 2H), 2.27 (t, 2H), 2.18 (s, 3H), 1.90 (s, 3H), 1.75 (m, 2H)

Example 28

N-(2-Chlorophenyl)sulfonyl-3-{3-[2-(4-aminoiminomethylphenyl)ethoxy]-5-methylphenylamino}butanoic acid×HCl The title compound was prepared according to the method described in Example 21 above from N-(2-chlorophenyl) sulfonyl-3-{3-[2-(4-aminoimino -methylphenyl)ethoxy]-5-methylphenylamino}butanoic acid, ethyl ester×HOAc (0.028 g; 0.045 mmol; from Example 26 above). After purification by preparative HPLC, the solid material was dissolved in a small volume of MeOH. HCl/aq (2M) was added and the resultant precipitate was filtered off, washed with water and dried to afford 0.016 g (63%) of a white solid.

LC-MS 530 (M+1)$^+$, 528 (M-1)$^-$ $^1$H NMR (400 MHz; CD$_3$OD): δ7.83 (d, 2H), 7.73 (d, 1H), 7.55–7.62 (several peaks, 2H), 7.71 (d, 2H), 7.33–7.40 (m, 1H), 6.62 (t, 1H), 6.57 (t, 1H), 6.43 (t, 1H), 4.10 (t, 2H), 3.83 (t, 2H), 3.08 (t, 2H), 2.20 (t, 2H), 2.18 (s, 3H), 1.81 (m, 2H)

Example 29

N-(2-Chlorophenyl)sulfonyl-4-{3-[2-(4-aminoiminomethylphenyl)ethoxy]-5-methylphenylamino}pentanoic acid, ethyl ester× HOAc (i) N-(2-Chlorophenyl)sulfonyl-4-{3-[2-(4-cyanophenyl)ethoxy]-5-methyl-phenylamino}pentananoic acid, ethyl ester The sub-title compound was prepared according to the method described in Example 26(ii) above from 3-[2-(4-cyanophenyl)-ethoxy]-5-methylphenyl-2-chlorobenzenesulfonamide (0.171 g; 0.40 mmol; from Example 26(i) above) and ethyl 4-bromopentanoate (95 μL; 0.6 mmol). Yield: 0.189 g (85%).

$^1$H NMR (400 MHz; CDCl$_3$): δ7.84 (dd, 1H), 7.62 (d, 2H), 7.52 (dd, 1H), 7.42 (m, 1H), 7.38 (d, 2H), 7.23 (m, 1H), 6.67–6.70 (m, 3H), 4.07–4.15 (several peaks, 4H), 3.91 (t, 2H), 3.10 (t, 2H), 2.31 (t, 2H), 2.21 (s, 3H), 1.69 (m, 2H), 1.53 (m, 2H), 1.22 (t, 3H)

(ii) N-(2-Chlorophenyl)sulfonyl-4-{3-[2-(4-ethoxyiminomethylphenyl)-ethoxy]-5-methylphenylamino}pentanoic acid ethyl ester×HCl The sub-title compound was prepared according to the method described Example 19(iii) above from N-(2-chlorophenyl)sulfonyl-4-{3-[2-(4-cyano-phenyl)ethoxy]-5-methylphenylamino}pentanoic acid, ethyl ester (0.189 g, 0.34 mmol; from step (i) above) in a quantitative yield.

$^1$H NMR (500 MHz; CDCl$_3$): δ12.5 (bs, 1H), 11.8 (bs, 1H), 8.35 (d, 2H), 7.82 (dd, 1H), 7.40–7.50 (several peaks, 4H), 7.23 (m, 1H), 6.58 (t, 1H), 6.55 (t, 1H), 6.50 (t, 1H), 4.95 (q, 2H), 4.02–4.10 (several peaks, 4H), 3.89 (t, 2H), 3.10 (t, 2H), 2.30 (t, 2H), 2.20 (s, 3H), 1.70 (m, 2H), 1.62 (t, 3H) 1.53 (m, 2H), 1.22 (t, 3H)

(iii) N-(2-Chlorophenyl)sulfonyl-4-{3-[2-(4-aminoiminomethylphenyl)-ethoxy]-5-methylphenylamino}pentanoic acid, ethyl ester× HOAc The title compound was prepared according to the method described Example 19(iv) above from N-(2-chlorophenyl) sulfonyl-4-{3-[2-(4-ethoxy-iminomethylphenyl)ethoxy]-5-methylphenylamino}pentanoic acid, ethyl ester×HCl (0.22 g; 0.34 mmol; from step (ii) above). Yield: 0.070 g (33%).

LC-MS 572 (M+1)$^+$ $^1$H NMR (400 MHz; CD$_3$OD): δ7.79 (dd, 1H), 7.76 (d, 2H), 7.50–7.60 (several peaks, 4H), 7.33 (m, 1H), 6.62 (t, 1H), 6.58 (m, 2H), 4.15 (t, 2H), 4.05 (q, 2H), 3.83 (t, 2H), 3.13 (t, 2H), 2.30 (t, 2H), 2.18 (s, 3H), 1.90 (s, 3H), 1.67 (m, 2H), 1.48 (m, 2H), 1.19 (t, 3H)

Example 30

4-{3-[2-(4-Aminoiminomethylphenyl)ethoxy]-N-(2-chlorophenyl)sulfonyl-5-methylphenylamino}pentanamide×HOAc The title compound was prepared according to the method described in Example 27 above from N-(2-chlorophenyl) sulfonyl-4-{3-[2-(4-aminoimino-methylphenyl)ethoxy]-5-methylphenylamino}pentanoic acid, ethyl ester×HOAc (0.022 g; 0.035 mmol; from Example 29 above). Yield: 0.009 g (42%).

LC-MS 543 (M+1)$^+$ $^1$H NMR (400 MHz; CD$_3$OD): δ7.79 (dd, 1H), 7.76 (d, 2H), 7.50–7.60 (several peaks, 4H), 7.32 (m, 1H), 6.62 (t, 1H), 6.58 (t, 1H), 6.55 (t, 1H), 4.13 (t, 2H), 3.82 (t, 2H), 3.12 (t, 2H), 2.19 (t, 2H), 2.18 (s, 3H), 1.90 (s, 3H), 1.67 (m, 2H), 1.48 (m, 2H)

Example 31

N-(2-Chlorophenyl)sulfonyl-4-{3-[2-(4-aminoiminomethylphenyl)ethoxy]-5-methylphenylamino}pentanoic acid×HCl The title compound was prepared according to the method described Example 28 above from N-(2-chlorophenyl)

sulfonyl-4-{3-[2-(4-aminoimino-methylphenyl)ethoxy]-5-methylphenylamino}pentanoic acid, ethyl ester×HOAc (0.026 g; 0.041 mmol; from Example 29 above). Yield: 0.016 g (46%).

LC-MS 544 (M+1)$^+$ $^1$H NMR (400 MHz; CD$_3$OD): δ7.90 (d, 2H), 7.74 (dd, 1H), 7.50–7.60 (several peaks, 4H), 7.40 (m, 1H), 6.63 (t, 1H), 6.58 (t, 1H), 6.43 (t, 1H), 4.12 (t, 2H), 3.82 (t, 2H), 3.12 (t, 2H), 2.33 (t, 2H), 2.20 (s, 3H), 1.75 (m, 2H), 1.48 (m, 2H)

Example 32

N-(2-Chlorophenyl)sulfonyl-5-{3-[2-(4-aminoiminomethylphenyl)ethoxy]-5-methylphenylamino}hexanoic acid, ethyl ester× HOAc (i) N-(2-Chlorophenyl)sulfonyl-5-{3-[2-(4-cyanophenyl)ethoxy]-5-methyl-phenylamino}hexanoic acid, ethyl ester The sub-title compound was prepared according to the method described in Example 26(ii) above from 3-[2-(4-cyanophenyl)ethoxy]-5-methylphenyl-2-chlorobenzenesulfonamide (0.150 g; 0.35 mmol; from Example 26(i) above) and ethyl 5-bromohexanoate (75 μL; 0.42 mmol). Yield: 0.185 g (93%).

$^1$H NMR (400 MHz; CDCl$_3$): δ7.83 (dd, 1H), 7.61 (d, 2H), 7.50 (dd, 1H), 7.42 (m, 1H), 7.38 (d, 2H), 7.26 (m, 1H), 6.67–6.70 (m, 3H), 4.07–4.15 (several peaks, 4H), 3.78 (t, 2H), 3.10 (t, 2H), 2.27 (t, 2H), 2.20 (s, 3H), 1.59 (m, 2H), 1.50 (m, 2H), 1.38 (m, 2H), 1.25 (t, 3H).

(ii) N-(2-Chlorophenyl)sulfonyl-5-{3-[2-(4-ethoxyiminomethylphenyl)-ethoxy]-5-methylphenylamino}hexanoic acid, ethyl ester×HCl The sub-title compound was prepared according to the method described Example 19(iii) above from N-(2-chlorophenyl)sulfonyl-5-{3-[2-(4-cyano-phenyl)ethoxy]-5-methylphenylamino}hexanoic acid, ethyl ester (0.185 g; 0.32 mmol) from step (i) above in a quantitative yield.

$^1$H NMR (500 MHz; CDCl$_3$): δ12.5 (bs, 1H), 11.8 (bs, 1H), 8.35 (d, 2H), 7.80 (dd, 1H), 7.40–7.50 (several peaks, 4H), 7.23 (m, 1H), 6.58 (t, 1H), 6.55 (t, 1H), 6.48 (t, 1H), 4.92 (q, 2H), 4.00–4.10 (several peaks, 4H), 3.79 (t, 2H), 3.10 (t, 2H), 2.22 (t, 2H), 2.19 (s, 3H), 1.70 (m, 2H), 1.52–1.60 (several peaks, 5H), 1.48 (m, 2H), 1.35 (m, 2H), 1.21 (t, 3H)

(iii) N-(2-Chlorophenyl)sulfonyl-5-{3-[2-(4-aminoiminomethylphenyl)-ethoxy]-5-methylphenylamino}hexanoic acid, ethyl ester× HOAc The title compound was prepared according to the method described in Example 19(iv) above from N-(2-chlorophenyl)sulfonyl-5-{3-[2-(4-ethoxy-iminomethylphenyl)ethoxy]-5-methylphenylamino }hexanoic acid, ethyl ester×HCl (0.21 g, 0.34 mmol; from step (ii) above). Yield: 0.11 g (74%).

LC-MS 586 (M+1)$^+$ $^1$H NMR (500 MHz; CD$_3$OD): δ7.79 (dd, 1H), 7.76 (d, 2H), 7.50–7.60 (several peaks, 4H), 7.35 (m, 1H), 6.62 (t, 1H), 6.58 (m, 2H), 4.16 (t, 2H), 4.10 (q, 2H), 3.83 (t, 2H), 3.15 (t, 2H), 2.28 (t, 2H), 2.19 (s, 3H), 1.90 (s, 3H), 1.58 (m, 2H), 1.47 (m, 2H), 1.40 (m, 2H), 1.22 (t, 3H)

Example 33

N-(2-Chlorophenyl)sulfonyl-5-{3-[2-(4-aminoiminomethylphenyl)ethoxy]-5-methylphenylamino}hexanamide×HOAc The title compound was prepared according to the method described in Example 27 above from N-(2-chlorophenyl) sulfonyl-5-{3-[2-(4-aminoimino-methylphenyl)ethoxy]-5-methylphenylamino}hexanoic acid, ethyl ester×HOAc (0.020 g; 0.031 mmol; from Example 32 above). Yield: 0.010 g (52%).

LC-MS 557 (M+1)$^+$ $^1$H NMR (400 MHz; CD$_3$OD): δ7.79 (dd, 1H), 7.76 (d, 2H), 7.50–7.60 (several peaks, 4H), 7.32 (m, 1H), 6.62 (t, 1H), 6.58 (t, 1H), 6.55 (t, 1H), 4.13 (t, 2H), 3.81 (t, 2H), 3.12 (t, 2H), 2.19 (2, 3H), 2.17 (t, 2H), 1.90 (s, 3H), 1.56 (m, 2H), 1.46 (m, 2H), 1.39 (m, 2H)

Example 34

N-(2-Chlorophenyl)sulfonyl-5-{3-[2-(4-aminoiminomethylphenyl)ethoxy]-5-methylphenylamino}hexanoic acid×HOAc The title compound was prepared according to the method described in Example 21 above from N-(2-chlorophenyl)sulfonyl-5-{3-[2-(4-aminoimino-methylphenyl)ethoxy]-5-methylphenylamino}hexanoic acid, ethyl ester×HOAc (0.040 g; 0.062 mmol) from Example 32 above. Yield: 0.026 g (68%).

ESI-MS 558 (M+1)$^+$, 556 (M−1)$^−$ $^1$H NMR (400 MHz; CD$_3$OD): δ7.82 (dd, 1H), 7.78 (d, 2H), 7.50–7.60 (several peaks, 4H), 7.35 (m, 1H), 6.62 (t, 1H), 6.57 (t, 1H), 6.52 (t, 1H), 4.12 (t, 2H), 3.81 (t, 2H), 3.12 (t, 2H), 2.19 (s, 3H), 1.90 (s, 3H), 1.56 (m, 2H), 1.46 (m, 2H), 1.39 (m, 2H)

Example 35

N-Phenylsulfonyl-3-[2-(4-aminoiminomethylphenyl) ethoxy]phenylamino-acetic acid, ethyl ester×HOAc (i) N-Phenylsulfonyl-3-[2-(4-cyanophenyl)ethoxy] phenylaminoacetic acid, ethyl ester N-{3-[2-(4-Cyanophenyl)ethoxy]phenyl}benzenesulfonamide (0.179 g; 0.47 mmol; from Example 1(iv) above), K$_2$CO$_3$ (0.082 g; 0.59 mmol) and ethyl bromoacetate (63 μL; 0.57 mmol) were stirred in DMF (10 mL) for 1 hour at room temperature, then 1 hour at 60° C. The mixture was filtered and the solvent removed in vacuo. The residue was dissolved in EtOAc and washed with water. The aqueous phase was extracted with EtOAc. The combined organic portions were dried (Na$_2$SO$_4$) and the solvent evaporated to afford the sub-title compound in a quantitative yield.

FAB-MS 465 (M+1)$^+$ (ii) N-(2-Phenyl)sulfonyl-3-[2-(4-aminoiminomethylphenyl)ethoxy]phenyl-aminoacetic acid, ethyl ester×HOAc Prepared according to the method described Example 1(v) and 1(vi) above from N-(2-chlorophenyl)sulfonyl-3-[2-(4-cyanophenyl)ethoxy]phenyl-aminoacetic acid, ethyl ester (0.225 g, 0.47 mmol; from step (i) above), which resulted only in a ca. 50% conversion ($^1$H NMR). The material was thus subjected, without further purification, to the reaction conditions as described in Example 1(vi) above. Purification by preparative HPLC (50% CH$_3$CN:0.1M NH$_4$OAc/aq)) afforded the title compound. The overall yield was 0.060 g (24%).

FAB-MS 482 (M+1)$^+$ $^1$H NMR (300 MHz; CD$_3$OD): δ7.76 (d, 2H), 7.50–7.70 (several peaks, 7H), 7.15 (m, 1H), 6.80–6.90 (several peaks, 2H), 6.63 (t, 1H), 4.40 (s, 2H), 4.05–4.20 (several peaks, 4H), 3.15 (t, 2H), 1.90 (s, 3H), 1.21 (t, 3H)

Example 36

N-Phenylsulfonyl-3-[2-(4-aminoiminomethylphenyl) ethoxy]phenylamino-acetic acid×HCl Aqueous NaOH (1.6 mL; 1M, 0.16 mmol) was added to a solution of N-phenylsulfonyl-3-[2-(4-aminoiminomethylphenyl)ethoxy]phenylaminoacetic acid, ethyl ester×HOAc (0.041 g, 0.079 mmol; from Example 35 above) in MeOH (3 mL) and the mixture was stirred overnight. Aqueous 1M HCl was added and the resultant precipitate was filtered off and dried, affording 0.016 g (41%) of the title compound.

LC-MS 454 (M+1)$^+$, 452 (M−1)$^-$; FAB-MS 454 (M+1)$^+$ $^1$H NMR (400 MHz; CD$_3$OD): δ7.73 (d, 2H), 7.55–7.65 (several peaks, 3H), 7.42–7.55 (several peaks, 4H), 7.08 (t, 1H), 6.82 (t, 1H), 6.75 (dd, 1H), 6.63 (dd, 1H), 4.20 (t, 2H), 4.17 (s, 2H), 3.15 (t, 2H)

Example 37

N-{3-[2-(4-Aminoiminomethylphenyl)ethoxy] phenyl}-N-(2-hydroxyethyl)-benzenesulfonamide× HOAc (i) N-{3-[2-(4-Cyanophenyl)ethoxy]phenyl}-N-(2-hydroxyethyl)-benzene-sulfonamide N-{3-[2-(4-cyanophenyl)ethoxy] phenyl}benzenesulfonamide (0.093 g; 0.246 mmol; from Example 1(iv) above), K$_2$CO$_3$ (0.047 g, 0.34 mmol), 2-chloroethanol (0.028 g; 0.34 mmol) and NaI (0.052 g; 0.34 mmol) were stirred in DMF (4 mL) for 24 hours at 100° C. The solvent was removed in vacuo. The residue was dissolved in water and extracted twice with EtOAc. The combined organic portions were washed with brine, dried (Na$_2$SO$_4$) and the solvent evaporated. Purification by flash chromatography (SiO$_2$; toluene:EtOAc 10:0, 9:1, 8:2, 6:4) afforded 0.047 g (45%) of the sub-title compound.

$^1$H NMR (300 MHz; CDCl$_3$): δ7.55–7.65 (several peaks, 4H), 7.40 (d, 2H), 7.15–7.30 (several peaks, 4H), 6.83 (dd, 1H), 6.73 (t, 1H), 6.55 (dd, 1H), 4.15 (t, 2H), 3.67 (m, 4H), 3.15 (t, 2H)

(ii) N-{3-[2-(4-Amino(hydroxyimino)methylphenyl) ethoxy]phenyl}-N-(2-hydroxyethyl)-benzenesulfonamide N-{3-[2-(4-Cyanophenyl)ethoxy]phenyl}-N-(2-hydroxyethyl)-benzene-sulfonamide (0.046 g, 0.108 mmol; from step (i) above), hydroxylamine hydrochloride (0.010 g, 0.15 mmol) and triethylamine (26 µL, 0.18 mmol) were heated to reflux for 5 hours. Evaporation in vacuo and flash chromatography afforded 0.033 g (67%) of the sub-title compound.

FAB-MS 456 (M+1)$^+$ (iii) N-{3-[2-(4-Aminoiminomethylphenyl)ethoxy] phenyl}-N-(2-hydroxy -ethyl)-benzenesulfonamide× HOAc A suspension of N-{3-[2-(4-amino(hydroxyimino) methylphenyl)ethoxy]-phenyl}-N-(2-hydroxyethyl)-benzenesulfonamide (0.033 g, 0.072 mmol; from step (ii) above), Pd (0.011 g; 10% on charcoal), HOAc (21 µL; 0.36 mmol), in EtOH (10 mL) and water (0.5 mL) was stirred under an atmosphere of H$_2$(g) for 6 hours. After filtration through Celite, the solvent was removed in vacuo and the residue was purified by preparative HPLC (50% CH$_3$CN:0.1M NH$_4$OAc/aq) to afford the title compound. Yield: 0.010 g (28%).

LC-MS 440 (M+1)$^+$ $^1$H NMR (300 MHz; D$_2$O): δ7.45–7.80 (several peaks, 9H), 7.30 (t, 1H), 6.97 (dd, 1H), 6.80 (dd, 1H), 6.55 (t, 1H), 4.22 (t, 2H), 3.72 (t, 2H), 3.55 (t, 2H), 3.13 (t, 2H), 1.98 (s, 3H)

$^{13}$C NMR (75 MHz; D$_2$O): δ167.2, 159.1, 146.2, 139.8, 136.8, 134.5, 130.9, 130.5, 130.0, 128.5, 128.1, 126.6, 122.9, 116.7, 116.0, 69.2, 59.2, 53.5, 35.2

Example 38

N-{3-[2-(4-Aminoiminomethylphenyl)ethoxy] phenyl}-N-(dimethyloxo-phosphinylmethyl)-benzenesulfonamide×HOAc (i) N-{3-[2-(4-Cyanophenyl)ethoxy]phenyl}-N-(dimethyloxophosphinyl-methyl)-benzenesulfonamide N-{3-[2-(4-Cyanophenyl)ethoxy] phenyl}benzenesulfonamide (0.224g; 0.59 mmol; from Example 1(iv) above), K$_2$CO$_3$ (0.111 g; 0.803 mmol) and chloromethyl dimethylphosphinoxide (0.090 g; 0.711 mmol) were stirred in DMF (10 mL) at 60° C. for 8 hours, 3 days at room temperature, and then 24 hours at 60° C. NaI (0.11 g; 0.73 mmol) was subsequently added and the mixture was heated to 100° C. for 1 day. The solvent was removed in vacuo and the residue dissolved in water. Extraction with EtOAc, drying (Na$_2$SO$_4$), evaporation in vacuo and purification by flash chromatography (SiO$_2$; toluene:EtOAc) afforded 0.125 g (45%) of the sub-title compound.

FAB-MS 469 (M+1)$^+$ $^1$H NMR (400 MHz; CDCl$_3$): δ7.58–7.63 (several peaks, 3H), 7.52 (d, 2H), 7.45 (t, 2H), 7.38 (d, 2H), 7.18 (t, 1H), 6.82 (dd, 1H), 6.68 (t, 1H), 6.55 (dd, 1H), 4.11 (t, 2H), 3.96 (d, 2H), 3.12 (t, 2H), 1.46 (d, 6H)

(ii) N-{3-[2-(4-Amino(hydroxyimino)methylphenyl) ethoxy]phenyl}-N-(dimethyloxophosphinylmethyl)-benzenesulfonamide Hydroxylamine hydrochloride (0.018 g; 0.26 mmol) and triethylamine (45 µL, 0.33 mmol) were added to a solution of N-{3-[2-(4-cyanophenyl)-ethoxy]phenyl}-N-(dimethyloxophosphinylmethyl)-benzenesulfonamide (0.090 g; 0.192 mmol; from step (i) above) in EtOH (6 mL). The mixture was heated at reflux for 3 hours, stirred at room temperature overnight and then refluxed for 1 hour. Evaporation of the solvent in vacuo and flash chromatography (SiO$_2$; EtOAc:MeOH (9:1)) afforded 0.054 g (56%) of the sub-title compound.

$^1$H NMR (400 MHz; CDCl$_3$): δ7.58–7.64 (several peaks, 3H), 7.53 (dd, 2H), 7.46 (t, 2H), 7.27 (d, 2H), 7.19 (t, 1H), 6.84 (ddd, 1H), 6.56–6.61 (m, 2H), 4.9 (bs, 2H), 4.10 (t, 2H), 3.95 (d, 2H), 3.08 (t, 2H), 1.45 (d, 6H)

(iii) N-{3-[2-(4-Aminoiminomethylphenyl)ethoxy] phenyl}-N-(dimethyl-oxophosphinylmethyl)-benzenesulfonamide×HOAc The title compound was prepared according to the method described in Example 37(iii) above from N-{3-[2-(4-amino (hydroxyimino)methylphenyl)-ethoxy]phenyl}-N-

(dimethyloxophosphinylmethyl)-benzenesulfonamide (0.012 g; 0.024 mmol; from step (ii) above). Yield: 0.009 g (69%).

$^1$H NMR (300 MHz; D$_2$O): δ7.70–7.80 (several peaks, 3H), 7.47–7.62 (several peaks, 6H), 7.30 (t, 1H), 6.97 (dd, 1H), 6.83 (dd, 2H), 6.65 (t, 1H), 4.1–4.3 (several peaks, 4H), 3.13 (t, 2H), 1.90 (s, 3H), 1.52 (d, 6H) $^{13}$C NMR (100 MHz; D$_2$O): δ177.8, 166.5, 158.6, 145.7, 139.9, 134.9, 134.4, 130.6, 130.0, 129.5, 127.9, 127.8, 125.9, 121.8, 116.4, 115.1, 68.6, 50.2 (d), 34.7, 21.2, 13.7 (d)

Example 39

2-Chlorobenzenesulfonic acid, 3-[2-(4-aminoiminomethylphenyl)ethoxy]-5-methylphenyl ester×HOAc (i) 3-[2-(4-Cyanophenyl)ethoxy]-5-methylphenol Triphenylphoshine (7.86 g; 30 mmol), 3,5-dihydroxytoluene (2.5 g; 20 mmol) and 2-(4-cyanophenyl)ethanol (4.41 g; 30 mmol) were dissolved in THF (50 mL). Diethylazodicarboxylate (5.22 g; 30 mmol; dissolved in THF (10 mL)), was added and the solution was stirred at room temperature overnight. The solvent was removed in vacuo and the white solid residue extracted with Et$_2$O. Purification by flash chromatography (SiO$_2$; toluene:EtOAc (10:1)) afforded 1.85 g (37%) of the sub-title compound as a white solid.

LC-MS 252 (M−1)$^−$ $^1$H NMR (500 MHz; CDCl3): δ7.60 (d, 2H), 7.39 (d, 2H), 6.28 (t, 1H), 6.26 (t, 1H), 6.20 (t, 1H), 4.95 (bs, 1H), 4.17 (t, 2H), 3.13 (t, 2H), 2.25 (s, 3H)

(ii) 3-[2-(4-Amino(hydroxyimino)methylphenyl)ethoxy]-5-methylphenol×HCl

3-[2-(4-Cyanophenyl)ethoxy]-5-methylphenol (0.39 g; 1.54 mmol; from step (i) above), hydroxylamine hydrochloride (0.128 g; 1.85 mmol) and triethylamine (281 μL; 2.00 mmol) were dissolved in EtOH (4 mL) and stirred at 80° C. for 20 minutes, then at room temperature overnight. The solvent was removed by evaporation and the residue was partitioned between dilute HCl/aq (pH 3) and CH$_2$Cl$_2$. The aqueous phase was washed with CH$_2$Cl$_2$ and stored in a refrigerator for 3 days. The precipitate which was obtained was filtered off and washed with Et$_2$O, yielding 0.33 g (75%) of the sub-title compound.

LC-MS 287 (M+1)$^+$ $^1$H NMR (400 MHz; CD$_3$OD): δ7.63 (d, 2H), 7.55 (d, 2H), 6.19 (m, 2H), 6.10 (t, 1H), 4.16 (t, 2H), 3.14 (t, 2H), 2.18 (s, 3H)

(iii) 3-[2-(4-aminoiminomethylphenyl)ethoxy]-5-methylphenol×HOAc

The sub-title compound was prepared using the method described in Example 37(iii) above from 3-[2-(4-amino(hydroxyimino)methylphenyl)-ethoxy]-5-methylphenol×HCl (0.27 g; 0.94 mmol; from step (ii) above). Yield: 0.265 g (85%).

LC-MS 271 (M+1)$^+$ $^1$H NMR (400 MHz; CD$_3$OD): δ7.78 (d, 2H), 7.53 (d, 2H), 6.21 (t, 1H), 6.18 (t, 1H), 6.13 (t, 1H), 4.13 (t, 2H), 3.11 (t, 2H), 2.18 (s, 3H), 2.0 (bs, 3H)

(iv) 3-[2-(4-amino{t-butoxycarbonylimino}methylphenyl)ethoxy]-5-methylphenol

Di-t-butylcarbonate (1.38 g; 6.3 mmol) was added to a suspension of 3-[2-(4-aminoiminomethylphenyl)ethoxy]-5-methylphenol×HCl (1.9 g; 6.0 mmol; from step (iii) above) and NaHCO$_3$ (1.51 g; 18 mmol) in THF (50 mL) and water (20 mL). After stirring overnight at room temperature, more di-t-butylcarbonate (0.263 g; 1.2 mmol) was added and the stirring continued for 6 hours. THF was removed in vacuo and the aqueous residue was extracted with MeOH:CH$_2$Cl$_2$ (1:4). The combined organic phases were washed with brine, dried (MgSO$_4$) and the solvent was evaporated. Purification by flash chromatography (SiO$_2$; EtOAc:hexane (1:2, 1:1)) afforded 1.8 g (81%) of the sub-title compound.

LC-MS 371 (M+1)$^+$, 369 (M−1)$^−$ $^1$H NMR (500 MHz; CD$_3$OD): δ7.76 (d, 2H), 7.41 (d, 2H), 6.21 (m, 2H), 6.14 (t, 1H), 4.14 (t, 2H), 3.10 (t, 2H), 2.20 (s, 3H), 1.52 (s, 9H)

(v) 2-Chlorobenzenesulfonic acid, 3-[2-(4-amino{t-butoxycarbonylimino}-methylphenyl)ethoxy]-5-methylphenyl ester To a solution of 3-[2-(4-amino{t-butoxycarbonylimino}methylphenyl)-ethoxy]-5-methylphenol (0.025 g; 67.5 mmol; from step (iv) above) and 4-dimethylaminopyridine (0.011 g; 88 mmol) in CH$_3$CN (5 mL) was added 2-chlorobenzenesulfonyl chloride (0.023 g; 81 mmol). The mixture was stirred at room temperature for one day, then filtered through a short plug of silica gel. After removal of the solvent in vacuo the residue was purified by flash chromatography (SiO$_2$; CH$_2$Cl$_2$:MeOH (1:0, 98:2)) yielding 0.018 g (49%) of the sub-title compound.

$^1$H NMR (500 MHz; CD$_3$OD): δ7.89 (dd, 1H), 7.75 (d, 2H), 7.70 (m, 1H), 7.66 (tt, 1H), 7.44 (dt, 1H), 7.35 (d, 2H), 6.62 (t, 1H), 6.46 (t, 1H), 6.38 (t, 1H), 4.07 (t, 2H), 3.04 (t, 2H), 2.19 (s, 3H), 1.51 (s, 9H)

(vi) 2-Chlorobenzenesulfonic acid, 3-[2-(4-aminoiminomethylphenyl)ethoxy]-5-methylphenyl ester×HOAc 2-Chlorobenzenesulfonic acid, 3-[2-(4-amino{t-butoxycarbonylimino}-methylphenyl)ethoxy]-5-methylphenyl ester (0.015 g; 0.028 mmol; from step (v) above) was added to EtOAc, presaturated with HCl(g), (3 mL) and the mixture was stirred at room temperature overnight. Evaporation of the solvent and purification by preparative HPLC (50% CH$_3$CH:0.1M NH$_4$OAc/aq) afforded the title compound: Yield: 0.010 g (80%).

LC-MS 444 (M+1)$^+$ $^1$H NMR (500 MHz; CD$_3$OD): δ7.90 (dd, 1H), 7.66–7.76 (several peaks, 4H), 7.52 (d, 2H), 7.45 (dt, 1H), 6.63 (t, 1H), 6.46 (t, 1H), 6.42 (t, 1H), 4.13 (t, 2H), 3.13 (t, 2H), 2.19 (s, 3H), 1.90 (s, 3H)

Example 40

Benzenesulfonic acid, 3-[2-(4-aminoiminomethylphenyl)ethoxy]phenyl ester× HOAc (i) Benzenesulfonic acid, 3-hydroxyphenyl ester The sub-title compound was prepared according to the method described in Example 2(i) above from 1,3-dihydroxybenzene (4.50 g; 40.9 mmol). Yield: 5.1 g (50%).

LC-MS 249 (M−1)$^−$ (ii) Benzenesulfonic acid, 3-[2-(4-cyanophenyl)ethoxy]phenyl ester The sub-title compound was prepared according to the method described in Example 2(ii) above from benzenesulfonic acid, 3-hydroxyphenyl ester (3.57 g; 14.3 mmol; from step (i) above). Yield: 3.7 g (69%).

$^1$H NMR (400 MHz; CDCl$_3$): δ7.85 (dd, 2H), 7.66 (tt, 1H), 7.61 (d, 2H), 7.52 (t, 2H), 7.36 (d, 2H), 7.13 (t, 1H), 6.75 (dd, 1H), 6.60 (t, 1H), 6.50 (dd, 1H), 4.11 (t, 2H), 3.11 (t, 2H)

(iii) Benzenesulfonic acid, 3-[2-(4-amino{hydroxyimino}methylphenyl)-ethoxy]phenyl ester The sub-title compound was prepared using the method described in Example 38(ii) above from benzenesulfonic acid, 3-[2-(4-cyanophenyl)-ethoxy]phenyl ester (0.100 g; 0.264 mmol; from step (ii) above). Yield: 0.095 g (88%).

LC-MS 413 (M+1)$^+$ (iv) Benzenesulfonic acid, 3-[2-(4-aminoiminomethylphenyl)ethoxy]phenyl ester× HOAc The title compound was prepared according to the method described in Example 37 (iii) from benzenesulfonic acid, 3-[2-(4-amino{hydroxyimino}-methylphenyl)ethoxy]phenyl ester (0.085 g; 0.21 mmol; from step (iii) above). Yield: 0.021 g (25%).

LC-MS 397 (M+1)$^+$ $^1$H NMR (400 MHz; CDCl$_3$): δ7.81 (m, 2H), 7.75 (d, 2H), 7.73 (tt, 1H), 7.58 (m, 2H), 7.53 (d, 2H), 7.16 (t, 1H), 6.80 (ddd, 1H), 6.53 (t, 1H), 6.50 ddd, 1H), 4.15 (t, 2H), 3.14 (t, 2H), 1.89 (s, 3H)

Example 41

2-Chloro-4-fluorobenzenesulfonic acid, 3-[2-(4-aminoiminomethylphenyl)-ethoxy]-5-chlorophenyl ester×HOAc (i) Chloro-3,5-dihydroxybenzene BBr$_3$ (26 mL; 0.275 mmol) was added to a solution of chloro-3,5-dimethyoxybenzene (10 g; 30 mmol) in CH$_2$Cl$_2$ (100 mL) at −70° C. The cooling bath was removed and the solution was stirred at room temperature for 4 days. After re-cooling to −70° C., MeOH was added (150 mL). After evaporation of the solvent, toluene was added and removed in vacuo. Purification by kugelrohr distillation afforded 9 g (100%) of the sub-title compound.

$^1$H NMR (300 MHz; CD$_3$OD): δ6.30 (d, 2H), 6.18 (t, 1H), 4.9 (bs, 1H)

(ii) 3-Chloro-5-[2-(4-cyanophenyl)ethoxy]phenol

Triphenylphoshine (32 g; 122 mmol) and diethylazodicarboxylate (19.2 mL; 122 mmol) were dissolved in CH$_2$Cl$_2$ (150 mL). Chloro-3,5-dihydroxybenzene (9.1 g; 63 mmol; from step (i) above) and 2-(4-cyanophenyl)ethanol (9.04 g; 61 mmol) were added and the solution was stirred at room temperature overnight. The mixture was diluted with Et$_2$O and filtered through Celite. The solvent was removed in vacuo. Purification, first by flash chromatography (SiO$_2$; CH$_2$Cl$_2$:MeOH), then by preparative HPLC (60% CH$_3$CN:0.1 M NH$_4$OAc/aq), afforded 3.55 g (21%) of the sub-title compound.

$^1$H NMR (300 MHz; CDCl$_3$): δ7.60 (d, 2H), 7.40 (d, 2H), 6.45–50 (m, 2H), 6.27 (t, 1H), 5.5 (bs, 1H), 4.15 (t, 2H), 3.12 (t, 2H)

(iii) 2-Chloro-4-fluorobenzenesulfonic acid, 3-[2-(4-cyanophenyl)ethoxy]-5-chlorophenyl ester 2-Chloro-4-fluorobenzenesulfonyl chloride (1.16 g; 5.0 mmol) was added to a cold solution (ice:water temperature) of 3-chloro-5-[2-(4-cyanophenyl)-ethoxy]phenol (0.689 g; 2.5 mmol; from step (ii) above) in pyridine (8 mL). The temperature was allowed to rise (slowly) to ambient overnight. The mixture was re-cooled (ice:water temperature) and ice was added to the reaction flask. After stirring for 4 hours, the pyridine was removed in vacuo. CH$_2$Cl$_2$ was then added and the organic layer was washed with aqueous KHSO$_4$ and water. Drying (MgSO$_4$), evaporation of the solvent and purification by flash chromatography (SiO$_2$; CH$_2$Cl$_2$) afforded 0.84 g (72%) of the sub-title compound.

$^1$H NMR (300 MHz; CDCl$_3$): δ7.97 (m, 1H), 7.60 (d, 2H), 7.30–7.40 (several peaks, 3H), 7.12 (m, 1H), 6.80 (t, 1H), 6.72 (t, 1H), 6.63 (t, 1H), 4.14 (t, 2H), 3.12 (t, 2H)

(iv) 2-Chloro-4-fluorobenzenesulfonic acid, 3-[2-(4-ethoxyiminomethyl-phenyl)ethoxy]-5-chlorophenyl ester×HCl The sub-title compound was prepared according to the method described Example 19(iii) above from 2-chloro-4-fluorobenzenesulfonic acid, 3-[2-(4-cyanophenyl)ethoxy]-5-chlorophenyl ester (0.576 g; 1.2 mmol; from step (iii) above) in a quantitative yield.

$^1$H NMR (400 MHz; CD$_3$OD): δ7.97–8.03 (several peaks, 3H), 7.63 (dd, 1H), 7.57 (d, 2H), 7.28 (m, 1H), 6.89 (t, 1H), 6.70 (t, 1H), 6.60 (t, 1H), 4.62 (q, 2H), 4.22 (t, 2H), 3.18 (t, 2H), 1.61 (t, 3H)

(v) 2-Chloro-4-fluorobenzenesulfonic acid, 3-[2-(4-aminoiminomethyl-phenyl)ethoxy]-5-chlorophenyl ester×HOAc The title compound was prepared according to the method described in Example 19(iv) above from 2-chloro-4-fluorobenzenesulfonic acid, 3-[2-(4-ethoxyiminomethylphenyl)ethoxy]-5-chlorophenyl ester× HCl (0.718 g; 1.3 mmol; from step (iv) above). Yield: 0.097 g (15%).

LC-MS 483 (M+1)$^+$ $^1$H NMR (400 MHz; CD$_3$OD): δ8.01 (m, 1H), 7.74 (d, 2H), 7.63 (dd, 1H), 7.53 (d, 2H), 7.28 (m, 1H), 6.89 (t, 1H), 6.70 (t, 1H), 6.61 (t, 1H), 4.20 (t, 2H), 3.16 (t, 2H), 1.88 (s, 3H)

Example 42

2-Chlorobenzenesulfonic acid, 3-[2-(4-aminoiminomethylphenyl)ethoxy]-5-methoxphenyl ester×HCl (i) 2-Chlorobenzenesulfonic acid, 3-hydroxy-5-methoxyphenyl ester Triethylamine (1.4 g; 14 mmol) was added to a solution of 3,5-dihydroxymethoxybenzene (2.0 g; 14 mmol) and 2-chlorobenzenesulfonyl chloride (3.3 g; 15.7 mmol) in pyridine (50 mL), and the mixture was stirred at room temperature overnight. Filtration through silica and purification by preparative HPLC afforded 0.998 g (22%) of the sub-title compound.

$^1$H NMR (500 MHz; CDCl$_3$): δ7.97 (dd, 1H), 7.55–7.62 (m, 2H), 7.38 (dt, 1H), 6.27 (m, 3H), 5.4 (bs, 1H), 3.68 (s, 3H)

(ii) 2-Chlorobenzenesulfonic acid, 3-[2-(4-cyanophenyl)ethoxy]-5-methoxy-phenyl ester The sub-title compound was prepared using the method described in Example 1 (ii) above from 2-chlorobenzenesulfonic acid, 3-hydroxy-5-methoxyphenyl ester (0.80 g; 2.5 mmol; from step (i) above). Purification by preparative HPLC afforded 0.50 g (45%) of the sub-title compound.

$^1$H NMR (400 MHz; CDCl$_3$): δ7.97 (dd, 1H), 7.55–7.62 (several peaks, 4H), 7.38 (dt, 1H), 7.35 (d, 2H), 6.32 (t, 1H), 6.28 (t, 1H), 6.25 (t, 1H), 4.08 (t, 2H), 3.68 (s, 3H), 3.08 (t, 2H)

(iii) 2-Chlorobenzenesulfonic acid, 3-[2-(4-ethoxyiminomethylphenyl)-ethoxy]-5-methoxyphenyl ester×HCl The sub-title compound was prepared using the method described in Example 3(iv) above from 2-chlorobenzenesulfonic acid and 3-[2-(4-cyanophenyl)ethoxy]-5-methoxyphenyl ester (0.50 g; 1.1 mmol; from step (ii) above) yielding 0.48 g (87%) of the sub-title compound.

LC-MS 490 (M+1)$^+$ (iv) 2-Chlorobenzenesulfonic acid, 3-[2-(4-aminoiminomethylphenyl)ethoxy]-5-methoxyphenyl ester×HCl The title compound was prepared using the method described in Example 3(v) above from 2-chlorobenzenesulfonic acid, 3-[2-(4-ethoxyiminophenyl)-ethoxy]-5-methoxyphenyl ester×HCl (0.48 g; 0.98 mmol; from step (iii) above). Freeze-drying with 1 molar equivalent of HCl afforded 0.39 g (80%) of the title compound.

LC-MS 461 (M+1)$^+$ $^1$H NMR (500 MHz; CD$_3$OD): δ7.92 (dd, 1H), 7.63–7.76 (several peaks, 4H), 7.52 (d, 2H), 7.47 (m, 1H), 6.34 (t, 1H), 6.24 (t, 1H), 6.19 (t, 1H), 4.14 (t, 2H), 3.69 (s, 3H), 3.13 (t, 2H)

Example 43

2-Chlorobenzenesulfonic acid, 3-[2-(4-aminoiminomethylphenyl)ethoxy]-5-ethylphenyl ester×HOAc (i) Ethyl-3,5-dimethoxybenzene The sub-title compound was prepared according to the procedure described in J. Chem. Soc. 859 (1949) from 3,5-dimethoxyacetophenone (5.0 g; 28 mmol). Yield 3.41 g (74%).

$^1$H NMR (400 MHz; CD$_3$OD): δ7.23 m,2H), 7.18 (t, 1H), 3.72 (s, 3H), 2.50 (q, 2H), 1.18 (t, 3H)

(ii) Ethyl-3,5-dihydroxybenzene

The sub-title compound was prepared according to the procedure described in J. Chem. Soc. 859 (1949) from ethyl-3,5-dimethoxybenzene (3.5 g; 21 mmol; from step (i) above). Yield 2.85 g (98%).

LC-MS 139 (M–1)$^-$ $^1$H NMR (400 MHz; CD$_3$OD): δ7.14 (m, 2H), 7.08 (t, 1H), 2.46 (q, 2H), 1.17 (t, 3H)

(iii) 3-[2-(4-Cyanophenyl)ethoxy]-5-ethylphenol

The sub-title compound was prepared using the method described in Example 39(i) above from ethyl-3,5-dihydroxybenzene (1.2 g; 8.69 mmol; from step (ii) above). Yield: 0.182 g (7.8%).

LC-MS 266 (M–1)$^-$ $^1$H NMR (400 MHz; CDCl$_3$): δ7.62 (d, 2H), 7.41 (d, 2H), 6.33 (t, 1H), 6.30 (t, 1H), 6.20 (t, 1H), 4.75 (bs, 1H), 4.17 (t, 2H), 3.15 (t, 2H), 2.57 (q, 2H), 1.22 (t, 3H)

(iv) 2-Chlorobenzenesulfonic acid, 3-[2-(4-ethoxyiminomethylphenyl)-ethoxy]-5-ethylphenyl ester×HCl 3-[2-(4-Cyanophenyl)ethoxy]-5-ethylphenol (0.040 g; 0.15 mmol; from step (iii) above) and triethylamine (0.018 g; 0.18 mmol) were dissolved in CH$_2$Cl$_2$ and 2-chlorobenzenesulfonyl chloride (0.050 g; 0.18 mmol) was added. After stirring for 2 hours, the mixture was washed with saturated K$_2$CO$_3$/aq and NaCl/aq. Filtration through a short plug of silica gel and evaporation of the solvent afforded 0.064 g of a solid. The solid material was stirred in EtOH (presaturated with HCl) overnight. Removal of excess HCl and the solvent in vacuo afforded 0.076 g (97%) of the sub-title compound.

LC-MS 488 (M+1)$^+$ (v) 2-Chlorobenzenesulfonic acid, 3-[2-(4-aminoiminomethylphenyl)ethoxy]-5-ethylphenyl ester×HOAc 2-Chlorobenzenesulfonic acid, 3-[2-(4-ethoxyiminomethylphenyl)ethoxy]-5-ethylphenyl ester× HCl (0.076 g; 0.15 mmol; from step (iv) above) was stirred in MeOH, presaturated with NH$_3$(S), (20 mL) for 1 day at room temperature. After evaporation in vacuo, the residue was purified by ion exchange chromatography to obtain the free amidine, which was freeze-dried from aqueous HOAc yielding 0.015 g (22%) of the title compound.

LC-MS 459 (M+1)$^+$

Example 44

N-{2-[2-(4-Aminoiminomethylphenyl)ethylthio]phenyl}-benzenesulfonamide×HCl (i) Amino-2-[2-(4-cyanophenyl)ethylthio]benzene 4-Toluenesulfonic acid, 2-(4-cyanophenyl)ethyl ester (1.9 g; 6.3 mmol; from Example 18(i) above) and K$_2$CO$_3$ (2.0 g) were added to a solution of 2-aminothiophenol (0.875 g; 7.0 mmol) in EtOH (20 mL). The mixture was heated to reflux for 48 hours, cooled, filtered and concentrated in vacuo to an oil which was dissolved in EtOAc (50 mL) and washed with water (25 mL). The organic portion was dried (MgSO$_4$) and concentrated. The residue was purified by flash chromatography (SiO$_2$; Et$_2$O:hexane (1:1)) to obtain 1.32 g (78%) of the sub-title product as a viscous oil.

$^1$H NMR (300 MHz; CDCl$_3$): δ7.57 (dd, 2H), 7.36 (dd, 2H), 7.26 (d, 2H), 7.14 (dt, 1H), 6.67–6.75 (m, 2H), 4.30 (bs, 2H), 3.05–3.10 (m, 2H), 2.95–3.05 (m, 2H)

(ii) N-{2-[2-(4-Aminoiminomethylphenyl)ethylthio]phenyl}-benzene-sulfonamide×HCl Benzenesulfonyl chloride (1.0 g; 5.7 mmol) was added dropwise over 10 minutes to a solution of amino-2-[2-(4-cyanophenyl)ethylthio]benzene (1.30 g; 5.11 mmol; from step (i) above) in a mixture of pyridine (2 mL) and CH$_2$Cl$_2$ (10 mL). After 2 hours stirring at room temperature the solution was diluted with CH$_2$Cl$_2$ (25 mL) and washed with aqueous 2M citric acid (25 mL). The organic portion was dried (MgSO$_4$) and the solvent removed in vacuo. The residue was filtered through a short column of silica with diethylether to afford a colourless oil (1.41 g). This oil was dissolved in a saturated solution of HCl in EtOH (30 mL) and maintained at room temperature for 48 hours. The solvent was removed in vacuo and the brown residue was dissolved in 7M methanolic ammonia. After a further 24 hours the solvent was evaporated and the product was purified by preparative HPLC (MeOH:CF$_3$COOH/aq (0.1M)) to obtain the trifluoroacetate, which was dissolved three times in MeOH, presaturated with HCl(g), and evaporated, to afford the title compound as a white solid. Yield: 0.63 g (28%).

mp 78–83° C.

LC-MS 412 (M+1)$^+$ $^1$H NMR (300 MHz; CDCl$_3$): δ9.60 (bs, 1H), 9.38 (s, 2H), 9.16 (s, 2H), 7.70–7.80 (m, 4H), 7.60–7.70 (m, 3H), 7.52 (d, 2H), 7.40 (dd, 2H), 7.22 (dt, 2H), 7.18 (dt, 1H), 6.94 (dd, 1H), 3.08 (t, 2H), 2.85 (t, 2H)

Example 45

5N-{2-[2-(4-Aminoiminomethylphenyl)ethylthio] phenyl}-2,4,5-trichloro-benzenesulfonamide× CF$_3$COOH (i) Amino-2-[2-(4-aminoiminomethylphenyl) ethylthio]benzene Amino-2-[2-(4-cyanophenyl)ethylthio]benzene (0.670 g; 2.63 mmol) from Example 44(i) above was dissolved in EtOH (presaturated with HCl; 2.5 mL), and stirred for 2 days. The solvent was evaporated, the residue was dissolved in toluene (50 mL) and concentrated in vacuo. The residue was dissolved in 7M methanolic ammonia at 0° C. and stirred overnight. The solvent was evaporated and crude product purified by preparative HPLC to afford the sub-title compound. Yield: 0.47 g (66%).

mp 228–30° C.

LC-MS 272 (M+H)$^+$ $^1$H NMR (300 MHz; DMSO-d$_6$): δ9.42 (s, 2H), 7.80 (d, 2H), 7.4–7.5 (m, 3H), 7.2–7.3 (m, 2H), 7.12 (t, 1H), 3.23 (t, 2H), 2.95 (t, 2H)

(ii)N-{2-[2-(4-Aminoiminomethylphenyl)ethylthio] phenyl}-2,4,5-trichloro-benzenesulfonamide× CF$_3$COOH Amino-2-[2-(4-aminoiminomethylphenyl)ethylthio] benzene (from step (i) above) was attached to a Wang resin (0.7 mmol functional groups (benzyl alcohol)/g) that had been modified with 4-nitrophenyl chloroformate as follows: Wang resin (0.100 g; 0.7 mmol/g; 0.07 mmol) was added to a solution of amino-2-[2-(4-aminoiminomethylphenyl) ethylthio]benzene (0.054 g; 0.20 mmol) in N-methylpyrrolidone (2 mL). Triethylamine (0.100 mL) was added and the mixture was gently stirred overnight at room temperature. The Wang resin was filtered off and washed five times with CH$_2$Cl$_2$.

The resin was then sulfonated and deprotected as follows: The resin (0.004 g; 0.7 mmol/g; 0.0028 mmol) was swelled with CH$_2$Cl$_2$ (0.100 mL) and a solution of 2,6-lutidine in CH$_2$Cl$_2$ (0.040 mL; 1.0 mol/L; 0.040 mmol) was added. A solution of 2,4,5-trichlorobenzenesulfonyl chloride (0.020 mL; 0.25 mol/L; 0.0050 mmol) was then added and the resultant mixture was shaken at room temperature overnight. More 2,4,5-trichlorobenzenesulfonyl chloride (0.040 mL; 0.25 mol/L; 0.010 mmol) was added and the reaction continued for 3 days. The resin was filtered off and washed five times with CH$_2$Cl$_2$. The title compound was cleaved off using a 20% solution of trifluoroacetic acid in CH$_2$Cl$_2$ (2×5 mL) and the solvents were removed in a vacuum desiccator. To estimate the yield, the purity was determined by LC-MS to 89%.

LC-MS: 516 (M+H)$^+$, 514 (M−1)$^-$

Example 46

N-{2-[2-(4-Aminoiminomethylphenyl)ethylthio] phenyl}-2-chloro-5-methoxybenzenesulfonamide× CF$_3$COOH The title compound was prepared according to the procedure described in Example 45 above, using 2-chloro-5-methoxyphenylsulfonyl chloride instead of 2,4,5-trichlorobenzenesulfonyl chloride. Yield: 87% (LC).

LC-MS: 476 (M+H)$^+$, 474 (M−1)$^-$

Example 47

N-{2-[2-(4-Aminoiminomethylphenyl)ethylthio] phenyl}-2,5-dibromo-benzenesulfonamide× CF$_3$COOH The title compound was prepared according to the procedure described in Example 45 above, using 2,5-dibromophenylsulfonyl chloride instead of 2,4,5-trichlorobenzenesulfonyl chloride. Yield: 81% (LC).

LC-MS: 570 (M+1)$^+$, 568 (M−1)$^-$

Example 48

N-{2-[2-(4-Aminoiminomethylphenyl)ethylthio] phenyl } -2 5-dichloro -benzenesulfonamide× CF$_3$COOH The title compound was prepared according to the procedure described in Example 45 above, using 2,5-dichlorophenylsulfonyl chloride instead of 2,4,5-trichlorobenzenesulfonyl chloride. Yield: 69% (LC).

LC-MS: 480 (M+H)$^+$, 478 (M−1)$^-$

Example 49

N-{2-[2-(4-Aminoiminomethylphenyl)-ethylthio]-phenyl}-2-methoxy-5-methylbenzenesulfonamide× CF$_3$COOH The title compound was prepared according to the procedure described in Example 45 above, using 2-methoxy-5-methylphenylsulfonyl chloride instead of 2,4,5-trichlorobenzenesulfonyl chloride. Yield: 84% (LC).

LC-MS: 456 (M+H)$^+$

Example 50

N-{2-[2-(4-Aminoiminomethylphenyl)ethylthio] phenyl}-2,3,5,6-tetramethylbenzenesulfonamide× CF$_3$COOH The title compound was prepared according to the procedure described in Example 45 above, using 2,3,5,6-tetramethylphenylsulfonyl chloride instead of 2,4,5-trichlorobenzenesulfonyl chloride. Yield: 84% (LC).

LC-MS: 468 (M+H)$^+$, 466 (M−1)$^-$

Example 51

N-{2-[2-(4-Aminoiminomethylphenyl)ethylthio] phenyl}-3,4-dimethoxy-benzenesulfonamide× CF$_3$COOH The title compound was prepared according to the procedure described in Example 45 above, using 3,4- dimethoxyphenylsulfonyl chloride instead of 2,4,5-trichlorobenzenesulfonyl chloride. Yield: 88% (LC).

LC-MS: 472 (M+H)+, 470 (M−1)−

Example 52

N-{2-[2-(4-Aminoiminomethylphenyl)ethylthio]phenyl}-3-bromo-benzenesulfonamide×CF₃COOH The title compound was prepared according to the procedure described in Example 45 above, using 3-bromophenylsulfonyl chloride instead of 2,4,5-trichlorobenzenesulfonyl chloride. Yield: 80% (LC).

LC-MS: 490 (M+H)+, 488 (M−1)−

Example 53

N-{2-[2-(4-Aminoiminomethylphenyl)ethylthio]phenyl}-3,4dibromobenzene-sulfonamide× CF₃COOH The title compound was prepared according to the procedure described in Example 45 above, using 3,4-dibromophenylsulfonyl chloride instead of 2,4,5-trichlorobenzenesulfonyl chloride. Yield: 75% (LC).

LC-MS: 570 (M+H)+, 568 (M−1)−

Example 54

N-{2-[2-(4-Aminoiminomethylphenyl)ethylthio]phenyl}-2-chloro-4-fluorobenzenesulfonamide× CF₃COOH The title compound was prepared according to the procedure described in Example 45 above, using 2-chloro-4-fluorophenylsulfonyl chloride instead of 2,4,5-trichlorobenzenesulfonyl chloride. Yield: 100% (LC).

LC-MS: 465 (M+H)+, 463 (M−1)−

Example 55

N-{2-[2-(4-Aminoiminomethylphenyl)ethylthio]phenyl}-5-bromo-2-methoxybenzenesulfonamide× CF₃COOH The title compound was prepared according to the procedure described in Example 45 above, using 5-bromo-2-methoxyphenylsulfonyl chloride instead of 2,4,5-trichlorobenzenesulfonyl chloride. Yield: 85% (LC).

LC-MS: 520 (M+H)+

Example 56

The title compounds of Examples 1 to 55 were tested in test A and/or B and/or test C above and were found to exhibit an $IC_{50}$ value and/or a $K_i$ value (as appropriate) of less than 0.3 μm.

Abbreviations

Ac=acyl
DCC=dicyclohexylcarbodiimide
DMF=dimethylformamide
EDC=1-(3-dimethylaminopropyl)-3-ethylcarbodiimide hydrochloride
Et=ethyl
Et₂O=diethyl ether
EtOAc=ethyl acetate
EtOH=ethanol
h=hours
HCl(g)=hydrogen chloride gas
HPLC=high performance liquid chromatography
HOAc=acetic acid
HOBt=N-hydroxybenzotriazole
LC=liquid chromatography
Me=methyl MeOH=methanol THF=tetrahydrofuran
prefixes n, s, i and t have their usual meanings: normal, iso, secondary and tertiary.

What is claimed is:

1. A compound of formula I,

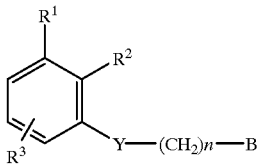

I wherein
one of $R^1$ and $R^2$ represents a structural fragment of formula Ia

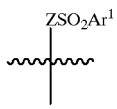

Ia and the other represents $R^4$;
Z represents O or $N(R^5)$;
$R^3$ represents one or more optional substituents selected from OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;
$R^4$ represents H, OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;
$Ar^1$ represents phenyl, $C_{1-3}$alkylphenyl, $C_{1-3}$alkyldiphenyl, $C_{3-7}$cycloalkyl, $C_{1-3}$-alkyl-$C_{3-7}$-cycloalkyl, $C_{1-3}$-alkyl-di-$C_{3-7}$-cycloalkyl, naphthyl, $C_{1-3}$alkylnaphthyl, thienyl, imidazolyl or isoxazolyl, all of which may be substituted by one or more substituent selected from OH, halo, cyano, nitro, $C(O)OR^6$, $C_{1-6}$alkoxy or $C_{1-6}$alkyl (which two latter groups are optionally substituted and/or terminated by one or more halo or hydroxy group) or $N(R^7)R^8$;
$R^5$ represents H, $C_{1-6}$alkyl, phenyl or $C_{1-3}$alkylphenyl (which three latter groups are optionally substituted and/or terminated by one or more substituent selected from OH, halo, cyano, nitro, $C(O)OR^9$, $C(O)N(R^{10})R^{11}$, $P(O)(R^{12})R^{13}$, $P(O)(OR^{14})OR^{15}$, $S(O)_2(R^{16})R^{17}$, $S(O)_2N(R^{18})R^{19}$, $C_{1-6}$alkoxy or $C_{1-6}$ alkyl (which two latter groups are optionally substituted and/or terminated by one or more halo or hydroxy group) or $N(R^{20})R^{21}$);
Y represents O, S, S(O), $S(O)_2$ or $N(R^{22})$;
$R^{10}$ and $R^{11}$ independently represent H, $OR^{23}$, $C(O)R^{24}$, $OC(O)R^{25}$, $C(O)OR^{26}$, $C_{1-4}$alkyl, (which latter group is optionally substituted and/or terminated by one or more substituent selected from $C_{1-4}$alkyl, $OR^{27}$, $N(R^{28})R^{29}$, $C(O)OR^{30}$ $C(O)N(R^{31})R^{32}$, $P(O)(R^{33})R^{34}$, $P(O)(OR^{35})OR^{36}$ and $S(O)_2N(R^{37})R^{38}$), $-(CH_2CH_2O-)_pR^{39}$ or, together with the nitrogen atom to which they are attached, form a $C_{4-7}$ nitrogen-containing, aromatic or non-aromatic, ring which ring may contain a further heteroatom or group (as appropriate) selected from O, S and N(R$^{40}$) and may further be substituted by one or more substituent selected from C(O)R$^{41}$, C(O)OR$^{42}$ or C(O)N(R$^{43}$)R$^{44}$;

R$^{28}$, R$^{29}$, R$^{30}$, R$^{31}$, R$^{32}$ and R$^{40}$ independently represent H or C$_{1-6}$alkyl, which latter group is optionally substituted and/or terminated by one or more substituent selected from C(O)R$^{45}$, C(O)OR$^{46}$ or C(O)N(R$^{47}$)R$^{48}$;

at each occurance, R$^6$, R$^7$ and R$^8$ independently represent H or C$_{1-4}$alkyl; R$^9$R$^{12}$R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{33}$, R$^{34}$, R$^{35}$, R$^{36}$, R$^{37}$, R$^{38}$, R$^{39}$, R$^{41}$, R$^{42}$, R$^{43}$, R$^{44}$, R$^{45}$, R$^{46}$, R$^{47}$ and R$^{48}$ independently represent H or C$_{1-4}$alkyl;

n represents 0, 1, 2, 3 or 4;

p represents 1, 2, 3, 4, 5 or 6; and

B represents a structural fragment of formula Ib, Ic, Id or Ie

Ib
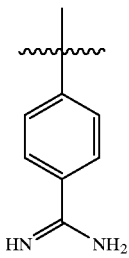

Ic
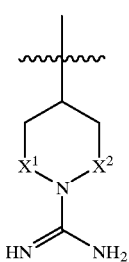

Id
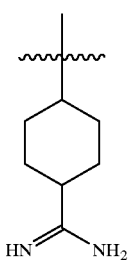

Ie
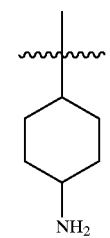

wherein
X$^1$ and X$^2$ independently represent a single bond or CH$_2$; or a pharmaceutically acceptable salt thereof, provided that when:
(i) B represents a structural fragment of formula Ic;
(ii) n represents 0 to 4;
(iii) either of R$^1$ or R$^2$ represents a structural fragment of formula Ia, and the other represents R$^4$ in which:

(a) Z represents O or N(Rs) (in which R$^5$ represents H, C$_{1-6}$alkyl, phenyl or C$_1$ alkylphenyl); and
(b) Ar$^1$ represents phenyl, optionally substituted by one or more substituents selected from OH, halo, cyano, nitro, C(O)OR$^6$ (in which R$^6$ is H or methyl), C$_{1-6}$alkoxy, C$_{1-2}$alkoxy substituted by F, C$_{1-6}$alkyl optionally substituted by hydroxy or N(R$^7$)R$^8$ (in which R$^7$ and R$^8$ both represent H or C$_{1-4}$alkyl or one of R$^7$ represents H and the other represents C$_{1-4}$alkyl); and (iv) R$^3$ and/or R$^4$ represents H, OH, halo, cyano, nitro, C(O)OR$^6$ (in which R$^6$ is H or C$_{1-4}$alkyl), C$_{1-4}$alkyl, C$_1$alkyl substituted by fluoro, C$_{1-6}$alkyl substituted by OH or C$_{1-4}$alkoxy; then Y does not represent O, S or N(R$^{22}$) (in which R$^{22}$ represents H or C$_{1-4}$alkyl).

2. A compound of formula I, as defined in claim 1, wherein, when B represents a structural fragment of formula Ib, Id, Ie or Ic in which latter fragment X$^1$ and X$^2$ both represent CH$_2$, then n represents 2.

3. A compound of formula I, as defined in one claim 1, wherein n represents 2.

4. A compound of formula I, as defined in claim 1, wherein R$^2$ represents a structural fragment of formula Ia and R$^1$ represents R$^4$.

5. A compound of formula I, as defined in claim 1, wherein Z represents O or N(R$^5$), in which latter case R$^5$ represents C$_{1-6}$alkyl terminated by C(O)N(R$^{10}$)R$^{11}$.

6. A compound of formula I, as defined in claim 1, wherein R$^3$ is not present, or represents methyl, chloro or methoxy.

7. A compound of formula I, as defined in claim 1, wherein Ar$^1$ represents substituted phenyl.

8. A compound of formula I, as defined in claim 1, wherein Y represents O.

9. A compound of formula I, as defined in claim 1, wherein B represents a structural fragment of formula Ib.

10. A compound as claimed in claim 1 which is:
N-{3-[2-(4-aminoiminomethylphenyl)ethoxy]phenyl}benzenesulfonamide; benzenesulfonic acid-{3-[2-(4-aminoiminomethylphenyl)ethoxy]-5-methyl}phenyl ester;
N-{3-[2-(4-aminoiminomethylphenyl)ethoxy]phenyl}-2-chlorobenzenesulfonamide;
N-{3-[2-(4-aminoiminomethylphenyl)ethoxy]phenyl}-2-cyanobenzene-sulfonamide;
N-{3-[2-(4-aminoiminomethylphenyl)ethoxy]phenyl}-2-fluorobenzene-sulfonamide;
N-{3-[2-(4-aminoiminomethylphenyl)ethoxy]phenyl}-2-(trifluoromethoxy)-benzenesulfonamide;
N-{3-[2-(4-aminoiminomethylphenyl)ethoxy]phenyl}-4-fluorobenzene-sulfonamide;
N-{3-[2-(4-aminoiminomethylphenyl)ethoxy]phenyl}-2,5-dimethylbenzene-sulfonamide;
N-{3-[2-(4-aminoiminomethylphenyl)ethoxy]phenyl}-5-chlorothiophene-2-sulfonamide;
N-{3-[2-(4-aminoiminomethylphenyl)ethoxy]phenyl}-1-methylimidazole-3-sulfonamide;
N-{3-[2-(4-aminoiminomethylphenyl)ethoxy]phenyl}-3,5-dimethylisoxazole-4-sulfonamide;
N-{3-[2-(4-aminoiminomethylphenyl)ethoxy]phenyl}benzylsulfonamide;
N-{3-[2-(4-aminoiminomethylphenyl)ethoxy]phenyl}-2,5-dichlorothiophene-3-sulfonamide;
N-{3-[2-(4-aminoiminomethylphenyl)ethoxy]-5-methylphenyl}-2-chlorobenzenesulfonamide;
N-{3-[2-(4-aminoiminomethylphenyl)ethoxy]-2-methylphenyl}-benzenesulfonamide;

N-{5-[2-(4-aminoiminomethylphenyl)ethoxy]-2-methylphenyl}benzene-sulfonamide;
N-{3-[2-(4-aminoiminomethylphenyl)ethoxy]-5-methylphenyl}benzene-sulfonamide;
N-{3-[2-(4-aminoiminomethylphenyl)ethylthio]phenyl}benzenesulfonamide;
N-(2-chlorophenyl)sulfonyl-3-[2-(4-aminoiminomethylphenyl)ethoxy]-5-methylphenylaminoacetic acid, ethyl ester;
N-(2-chlorophenyl)sulfonyl-3-[2-(4-aminoiminomethylphenyl)ethoxy]-5-methylphenylaminoacetamide;
N-(2-chlorophenyl)sulfonyl-3-[2-(4-aminoiminomethylphenyl)ethoxy]-5-methylphenylaminoacetic acid;
N-(2-chlorophenyl)sulfonyl-2-{3-[2-(4-aminoiminomethylphenyl)ethoxy]-5-methylphenylamino}propanoic acid, ethyl ester;
2-{3-[2-(4-aminoiminomethylphenyl)ethoxy]-N-(2-chlorophenyl)sulfonyl-5-methylphenylamino}propanamide;
N-(2-chlorophenyl)sulfonyl-2-{3-[2-(4-aminoiminomethylphenyl)ethoxy]-5-methylphenylamino}propanoic acid;
N-(2-chlorophenyl)sulfonyl-2-{3-[2-(4-aminoiminomethylphenyl)ethoxy]-5-methylphenylamino}propanoic acid, methyl ester;
N-(2-chlorophenyl)sulfonyl-3-{3-[2-(4-aminoiminomethylphenyl)ethoxy]-5-methylphenylamino}butanoic acid, ethyl ester;
3-{3-[2-(4-aminoiminomethylphenyl)ethoxy]-N-(2-chlorophenyl)sulfonyl-5-methylphenylamino}butanamide;
N-(2-chlorophenyl)sulfonyl-3-{3-[2-(4-aminoiminomethylphenyl)ethoxy]-5-methylphenylamino}butanoic acid;
N-(2-chlorophenyl)sulfonyl-4-{3-[2-(4-aminoiminomethylphenyl)ethoxy]-5-methylphenylamino}pentanoic acid, ethyl ester;
4-{3-[2-(4-aminoiminomethylphenyl)ethoxy]-N-(2-chlorophenyl)sulfonyl-5-methylphenylamino}pentanamide;
N-(2-chlorophenyl)sulfonyl-4-{3-[2-(4-aminoiminomethylphenyl)ethoxy]-5-methylphenylamino}pentanoic acid;
N-(2-chlorophenyl)sulfonyl-5-{3-[2-(4-aminoiminomethylphenyl)ethoxy]-5-methylphenylamino}hexanoic acid, ethyl ester;
5-{3-[2-(4-aminoiminomethylphenyl)ethoxy]-N-(2-chlorophenyl)sulfonyl-5-methylphenylamino}pentanamide;
N-(2-chlorophenyl)sulfonyl-5-{3-[2-(4-aminoiminomethylphenyl)ethoxy]-5-methylphenylamino}hexanoic acid;
N-phenylsulfonyl-3-[2-(4-aminoiminomethylphenyl)ethoxy]phenylamino-acetic acid, ethyl ester;
N-phenylsulfonyl-3-[2-(4-aminoiminomethylphenyl)ethoxy]phenylamino-acetic acid;
N-{3-[2-(4-aminoiminomethylphenyl)ethoxy]phenyl}-N-(2-hydroxyethyl)-benzenesulfonamide;
N-{3-[2-(4-aminoiminomethylphenyl)ethoxy]phenyl}-N-(dimethyloxo-phosphinylmethyl)-benzenesulfonamide;
2-chlorobenzenesulfonic acid, 3-[2-(4-aminoiminomethylphenyl)ethoxy]-5-methylphenyl ester;
benzenesulfonic acid, 3-[2-(4-aminoiminomethylphenyl)ethoxy]phenyl ester;
2-chloro-4-fluorobenzenesulfonic acid, 3-[2-(4-aminoiminomethylphenyl)-ethoxy]-5-chlorophenyl ester;
2-chlorobenzenesulfonic acid, 3-[2-(4-aminoiminomethylphenyl)ethoxy]-5-methoxyphenyl ester;
2-chlorobenzenesulfonic acid, 3-[2-(4-aminoiminomethylphenyl)ethoxy]-5-ethylphenyl ester;
N-{2-[2-(4-aminoiminomethylphenyl)ethylthio]phenyl}benzenesulfonamide;
N-{2-[2-(4-aminoiminomethylphenyl)ethylthio]phenyl}-2,4,5-trichloro-benzenesulfonamide;
N-{2-[2-(4-aminoiminomethylphenyl)ethylthio]phenyl}-2-chloro-5-methoxybenzenesulfonamide;
N-{2-[2-(4-aminoiminomethylphenyl)ethylthio]phenyl}-2,5-dibromo-benzenesulfonamide;
N-{2-[2-(4-aminoiminomethylphenyl)ethylthio]phenyl}-2,5-dichloro-benzenesulfonamide;
N-{2-[2-(4-aminoiminomethylphenyl)-ethylthio]-phenyl}-2-methoxy-5-methylbenzenesulfonamide;
N-{2-[2-(4-aminoiminomethylphenyl)ethylthio]phenyl}-2,3,5,6-tetramethylbenzenesulfonamide;
N-{2-[2-(4-aminoiminomethylphenyl)ethylthio]phenyl}-3,4-dimethoxy-benzenesulfonamide;
N-{2-[2-(4-aminoiminomethylphenyl)ethylthio]phenyl}-3-bromo-benzenesulfonamide;
N-{2-[2-(4-aminoiminomethylphenyl)ethylthio]phenyl}-3,4-dibromobenzene-sulfonamide;
N-{2-[2-(4-aminoiminomethylphenyl)ethylthio]phenyl}-2-chloro-4-fluorobenzenesulfonamide; or
N-{2-[2-(4-aminoiminomethylphenyl)ethylthio]phenyl}-5-bromo-2-methoxybenzenesulfonamide.

11. A compound of formula I, as defined in claim 1, provided that $R^1$ represents a structural fragment of formula Ia and $R^2$ represents $R^4$.

12. A compound of formula I, as defined in claim 1, provided that $Ar^1$ represents optionally substituted phenyl.

13. A compound of formula I, as defined in claim 1, provided that $R^5$ is not substituted by $P(O)(OR^{14})OR^{15}$, $S(O)_2(R^{16})R^{17}$ or $S(O)_2N(R^{18})R^{19}$.

14. A compound of formula I, as defined in claim 1, provided that $R^{10}$ and/or $R^{11}$ represent H or unsubstituted $C_{1-4}$alkyl.

15. A compound of formula I, as defined in claim 1, provided that Y represents O, S or $N(R^5)$.

16. A compound of formula I, as defined in claim 1, provided that B represents a structural fragment of formula Ib, Ic or Id.

17. A compound of formula I, as defined in claim 1, provided that $R^2$ represents a structural fragment of formula Ia and $R^1$ represents $R^4$.

18. A compound of formula I, as defined in claim 1, provided that $Ar^1$ does not represent optionally substituted phenyl.

19. A compound of formula I, as defined in claim 1, provided that $R^5$ is substituted by $P(O)(OR^{14})OR^{15}$, $S(O)_2(R^{16})R^{17}$ or $S(O)_2N(R^{18})R^{19}$.

20. A compound of formula I, as defined in claim 1, provided that $R^{10}$ and/or $R^{11}$ do not represent H or unsubstituted $C_{1-4}$alkyl.

21. A compound of formula I, as defined in claim 1, provided that Y represents S(O) or $S(O)_2$.

22. A compound of formula I, as defined in claim 1, provided that B represents a structural fragment of formula Ie.

23. A pharmaceutical formulation including a compound as defined in claim 1, or a pharmaceutically acceptable salt thereof, in admixture with a pharmaceutically acceptable adjuvant, diluent or carrier.

24. A compound as defined in claim 1, or a pharmaceutically acceptable salt thereof, for use as a pharmaceutical.

25. A compound as defined in claim 1, or a pharmaceutically acceptable salt thereof, for use in the treatment of a condition where inhibition of thrombin is required.

26. A compound as defined in claim 1, or a pharmaceutically acceptable salt thereof, for use in the treatment of thrombosis.

27. A compound of formula I as defined in claim 1, or a pharmaceutically acceptable salt thereof, for use as an anticoagulant.

28. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition.

29. A method as claimed in claim 28, wherein the condition is thrombosis.

30. A method as claimed in claim 28, wherein the condition is hypercoagulability in blood and tissues.

31. A process for the preparation of compounds of formula I which comprises:

(a) reaction of a compound of formula II,

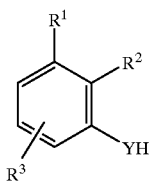
II wherein $R^1$, $R^2$, $R^3$ and Y are as defined in claim 1 with a compound of formula III,

III wherein $L^1$ represents a suitable leaving group and n and B are as defined in claim 1;

(b) reaction of a compound of formula IV,

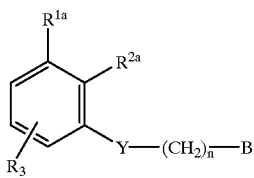
IV wherein one of $R^{1a}$ and $R^{2a}$ represents ZH and the other represents $R^4$, and Z, $R^3$, $R^4$, Y, n and B are as defined in claim 1 with a compound of formula V,

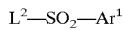
V wherein $L^2$ is a suitable leaving group and $Ar^1$ is as defined in claim 1;

(c) for compounds of formula I in which Y represents O or S, reaction of a compound of formula VI,

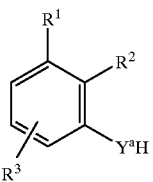
VI wherein $Y^a$ represents O or S and $R^1$, $R^2$ and $R^3$ are as defined in claim 1 with a compound of formula VII,

VII wherein n and B are as defined in claim 1;

(d) for compounds of formula I wherein B represents a structural fragment of formula Ib or Id, reaction of a compound of formula VIII,

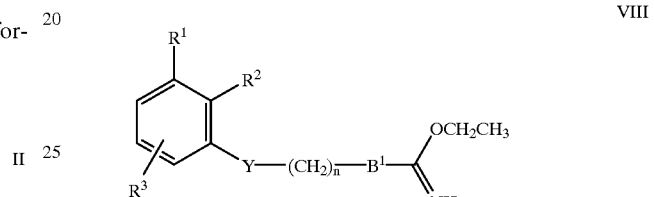
VIII wherein $B^1$ represents 1,4-phenylene or 1,4-cyclohexylene and $R^1$, $R^2$, $R^3$, Y and n are as defined in claim 1 with ammonia gas;

(e) for compounds of formula I wherein B represents a structural fragment of formula Ib or Id, reduction of a compound of formula IX,

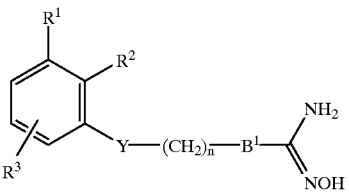
IX wherein $R^1$, $R^2$, $R^3$, Y and n are as defined in claim 1 and $B^1$ is as defined above;

(f) for compounds of formula I wherein B represents a structural fragment of formula Ib or Id, reaction of a compound of formula X,

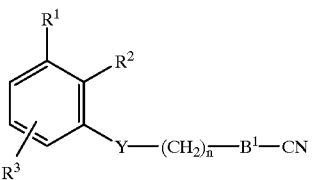
X wherein $R^1$, $R^2$, $R^3$, Y and n are as defined in claim 1 and $B^1$ is as defined above;

(g) for compounds of formula I wherein Y represents S(O) or $S(O)_2$, oxidation of a corresponding compound of formula I wherein Y represents S;

(h) for compounds of formula I wherein Z represents $N(R^5)$ and $R^5$ represents optionally substituted $C_{1-6}$alkyl, phenyl or $C_{1-3}$alkylphenyl, reaction of a corresponding compound of formula I wherein Z represents NH with a compound of formula XI, $$L^2-R^{5a} \quad\quad XI$$

wherein $R^{5a}$ represents optionally substituted $C_{1-6}$alkyl, phenyl or $C_{1-3}$alkylphenyl and $L^2$ is as defined above;

(i) for compounds of formula I wherein Z represents $N(R^5)$ and $R^5$ represents $C_{1-6}$alkyl, phenyl or $C_{1-3}$alkylphenyl, all of which are substituted and/or terminated by $C(O)N(R^{10})R^{11}$, reaction of a corresponding compound of formula I wherein $R^5$ represents $C_{1-6}$alkyl, phenyl or $C_{1-3}$alkylphenyl, all of which are substituted and/or terminated, by $C(O)OR^9$, and $R^9$ is as defined in claim 1, with a compound of formula XII, $$HN(R^{10})R^{11} \quad\quad XII$$

wherein $R^{10}$ and $R^{11}$ are as defined in claim 1;

(j) for compounds of formula I wherein Z represents $N(R^5)$ and $R^5$ represents $C_{1-6}$alkyl, phenyl or $C_{1-3}$alkylphenyl, all of which are substituted and/or terminated by $C(O)OH$, hydrolysis of a corresponding compound of formula I wherein $R^5$ represents $C_{1-6}$alkyl, phenyl or $C_{1-3}$alkylphenyl, all of which are substituted and/or terminated by $C(O)OR^9$ and $R^9$ represents $C_{1-4}$alkyl; or (k) for compounds of formula I wherein Z represents $N(R^5)$ and $R^5$ represents $(CH_2)_2C(O)OR^9$ and $R^9$ is as defined in claim 1, reaction of a corresponding compound of formula I wherein $R^5$ represents H with a compound of formula XIII, $$CH_2=CH-C(O)OR^9 \quad\quad XIII$$

wherein $R^9$ is as defined in claim 1.

\* \* \* \* \*